(12) United States Patent
Margolin et al.

(10) Patent No.: US 7,718,169 B2
(45) Date of Patent: May 18, 2010

(54) COMPOSITIONS AND METHODS FOR TREATING PANCREATIC INSUFFICIENCY

(75) Inventors: Alexey L. Margolin, Newton, MA (US); Bhami C. Shenoy, South Grafton, MA (US); Frederick T. Murray, Hanover, MA (US); Anthony Christopher Lee Stevens, Boston, MA (US)

(73) Assignee: Cystic Fibrosis Foundations Therapeutics, Inc., Bethesda, MD (US)

(*) Notice: Subject to any disclaimer, the term of this patent is extended or adjusted under 35 U.S.C. 154(b) by 1012 days.

(21) Appl. No.: 11/251,278

(22) Filed: Oct. 14, 2005

(65) Prior Publication Data

US 2006/0121017 A1 Jun. 8, 2006

Related U.S. Application Data

(60) Provisional application No. 60/618,764, filed on Oct. 14, 2004.

(51) Int. Cl.
A61K 38/54 (2006.01)

(52) U.S. Cl. .................................... 424/94.2

(58) Field of Classification Search ........................ None
See application file for complete search history.

(56) References Cited

U.S. PATENT DOCUMENTS

| | | | |
|---|---|---|---|
| 3,994,470 A | 11/1976 | Nakada et al. | |
| 4,079,125 A | 3/1978 | Sipos | |
| 4,659,667 A | 4/1987 | Brewer et al. | |
| 4,876,024 A | 10/1989 | Enomoto et al. | |
| 5,008,031 A | 4/1991 | Schulz et al. | |
| 5,290,694 A | 3/1994 | Nakanishi et al. | |
| 5,489,530 A | 2/1996 | Braatz et al. | |
| 5,614,189 A | 3/1997 | Huge-Jensen | |
| 5,618,710 A | 4/1997 | Navia et al. | |
| 5,645,832 A | 7/1997 | Braatz et al. | |
| 5,681,715 A | 10/1997 | Jorgensen et al. | |
| 5,719,048 A | 2/1998 | Nilsson et al. | |
| 5,731,280 A | 3/1998 | Nielsen et al. | |
| 5,750,104 A | 5/1998 | Sipos | |
| 5,767,066 A | 6/1998 | Barnwell | |
| 5,817,493 A | 10/1998 | Reetz et al. | |
| 5,849,296 A | 12/1998 | Navia et al. | |
| 5,892,013 A | 4/1999 | Svendsen et al. | |
| 5,928,640 A | 7/1999 | Mynott | |
| 5,932,212 A | 8/1999 | Khalaf | |
| 5,976,529 A | 11/1999 | Navia et al. | |
| 6,011,001 A | 1/2000 | Navia et al. | |
| 6,013,680 A | 1/2000 | Ogawa et al. | |
| 6,017,866 A | 1/2000 | Aehle et al. | |
| 6,030,798 A | 2/2000 | Braatz et al. | |
| 6,042,823 A | 3/2000 | Kimura et al. | |
| 6,051,220 A | 4/2000 | Scharpe | |
| 6,080,402 A | 6/2000 | Reetz et al. | |
| 6,140,475 A | 10/2000 | Margolin et al. | |
| 6,156,552 A | 12/2000 | Okkels et al. | |
| 6,541,606 B2 | 4/2003 | Margolin et al. | |
| 2001/0046493 A1 | 11/2001 | Margolin et al. | |
| 2003/0017144 A1 | 1/2003 | Margolin et al. | |
| 2004/0057944 A1 | 3/2004 | Galle et al. | |
| 2006/0128587 A1 | 6/2006 | Margolin et al. | |

FOREIGN PATENT DOCUMENTS

| | | |
|---|---|---|
| EP | 0387945 | 3/1993 |
| EP | 0506791 | 8/1993 |
| EP | 0600868 | 7/1999 |
| GB | 1442677 | 7/1976 |
| WO | 92/02617 | 2/1992 |
| WO | 96/38170 | 5/1996 |
| WO | 97/44445 | 11/1997 |
| WO | 98/46732 | 10/1998 |
| WO | 99/12959 | 3/1999 |
| WO | 99/55310 | 11/1999 |
| WO | WO 01/62280 | 8/2001 |
| WO | WO 02/060474 | 8/2002 |

OTHER PUBLICATIONS

Mascarenthas, "Treatment of gastrointestinal problems in cystic fibrosis." *Current Treatment Options in Gastroenterology*, 6:427-441 (2003).

Santini et al., "Comparison of two enteric coated microsphere preparations in the treatment of pancreatic exocrine insufficiency caused by cystic fibrosis," *Digest. Liver Dis.*, 32:406-411 (2000).

"Oral TheraCLEC-Total in cystic fibrosis subjects with exocrine pancreatic insufficiency"[Online] Dec. 8, 2005, XP002369915 Retrieved from the Internet: http://www.clinicaltrials.gov/ct/show/NCT00095732?order=1%20>%20[ retrieved%20on%202006-02-28].

"Altus pharmaceuticals presents results from ALTU-135 (Theraclec) Phase II study in cystic fibrosis patients with pancreatic insufficiency."[Online] Oct. 24, 2005, XP002369916 Retrieved from the Internet: URL:http:// http://www.altus.com/news-and-events/press-detail.cfm?id=33.

Borowitz et al., "Use of pancreatic enzyme supplements for patients with cystic fibrosis in the context of fibrosing colonopathy," *The Journal of Pediatrics*, 127:681-684 (1995).

Borowitz et al., "Use of fecal elastase-1 to classify pancreatic status in patients with cystic fibroris," *The Journal of Pediatrics*, 145:322-326 (2004).

(Continued)

*Primary Examiner*—Sandra E. Saucier
(74) *Attorney, Agent, or Firm*—Finnegan, Henderson, Farabow, Garrett & Dunner, LLP

(57) ABSTRACT

The present invention relates to compositions for the treatment of conditions, including pancreatic insufficiency. The compositions of the present invention comprise lipase, protease and amylase in a particular ratio that provides beneficial results in patients, such as those afflicted with pancreatic insufficiency. This invention also relates to methods using such compositions for the treatment of pancreatic insufficiency. The compositions specifically comprise crosslinked *Burkholderia cepacia* lipase crystals, *Aspergillus melleus* protease crystals and amorphous *Aspergillus oryzae* amylase in a ratio of about 1:1:0.15 USP units.

20 Claims, 7 Drawing Sheets

OTHER PUBLICATIONS

Bruno et al., "Comparative Effects of Adjuvant Cimetidine and Omprazole during Pancreatic Enzyme Replacement Therapy", *Digestive Diseases and Sciences*, 39(5):988-992 (1994).
Carpenter et al., "Rational Design of Stable Lyophilized Protein Formulations: Some Pratice Advice, *Pharmaceutical Research*" 14(8):969-975 (1997).
Case et al., "Enzyme Content and Acid Stability of Enteric-Coated Pancreatic Enzyme Products in vitro", *Pancreas*, 30(2):180-183 (2005).
DiMagno et al., "Chronic Pancreatitis", *The Pancreas: Biology, Pathobiology and Disease*, 2d Ed., V. Liang et al., eds., pp. 665-701 (1993).
Durie et al., "Uses and Abuses of Enzyme Therapy in Cystic Fibrosis", *Journal of the Royal Society of Medicine*, 91(34):2-3 (1998).
Fitzsimmons et al., "High-Dose Pancreatic-Enzyme Supplements and Fibrosing Colonopathy in Children with Cystic Fibrosis", *New England Journal of Medicine*, 336(18):1283-1289 (1997).
Francisco et al., "Ranitidine and Omeprazole as Adjuvant Therapy to Pancrealipase to Improve Fat Absorption in Patients with Cystic Fibrosis", *Journal of Pediatric Gastroenterology and Nutrition*, 35:79-83 (2002).
Fredrikzon et al., "Lingual Lipase: an Important Lipase in the Digestion of Dietary Lipids in Cystic Fibrosis?", *Pediatric Research*, 14:1387-1390 (1980).
Gaskin et al., "Improved Respiratory Prognosis in Cf Patients with Normal Fat Absorption", *Journal of Pediatrics*, 100(6):857-862 (1982).
Graham, "Pancreatic Enzyme Replacement: the Effect of Antacids or Cimetidine", *Digestive Diseases and Sciences*, 27(6):485-490 (1982).
Heijerman et al., "Omeprazole Enhances the Efficacy of Pancreatin (Pancrease) in Cystic Fibrosis", *Annals of Internal Medicine*, 114:200-201 (1991).
Kawchak et al., "Longitudinal, Prospective Analysis of Dietary Intake in Children with Cystic Fibrosis", *Journal of Pediatrics*, 129:119-129 (1996).
Kraisinger et al., "Clinical Pharmacology of Pancreatic Enzymes in Patients with Cystic Fibrosis and in vitro Performance of Microencapsulated Formulations", *Journal of Clinical Pharmacology*, 34:158-166 (1994).
Lankish, "Enzyme Treatment of Exocrine Pancreatic Insufficiency in Chronic Pancreatitis", *Digestion*, 54(2):21-29 (1993).
Lebenthal et al., "Enzyme Therapy for Pancreatic Insufficiency: Present Status and Future Needs", *Pancreas*, 9(1):1-12 (1994).
Littlewood et al., "Control of Malabsorption in Cystic Fibrosis", *Pediatric Drugs*, 2(3):205-222 (2000).
McPherson et al., "Crystallization of Macromolecules: General Principles," *Methods in Enzymology*, 114:112-120 (1985).
Gilliland, "A Biological Macromolecules Crystallization Database: A Basis for a Crystallization Strategy," *Journal of Crystal Growth*, 90:51-59 (1988).
Meyer, "Delivery of Pancreation in Microspere Preparations: Transit, Timing, Physiological Needs," *Pancreatic Enzymes in Health and Disease*, P.G. Lankisch, ed., 71-88 (1991).
Powell et al., "Colonic Toxicity from Pancreatins: a Contemporary Safety Issue", *Lancet*, 353:911-915 (1999).
Regan et al., "Comparative Effects of Antacids, Cimetidine and Enteric Coating on the Therapeutic Response to Oral Enzymes in Severe Pancreatic Insufficiency", *New England Journal of Medicine*, 297(16):854-858 (1977).
Rosenstein et al., "The Diagnosis of Cystic Fibrosis: A Consensus Statement", *Journal Pediatrics*, 132(4):589-595 (1998).
Rowe et al., "Mechanisms of Disease: Cystic Fibrosis", *New England Journal Medicine*, 352(19):1992-2001 (2005).
Saunders et al., "Inhibition of Gastric Secretion in Treatment of Pancreatic Insufficiency", *British Medical Journal*, 1:418-419 (1977).
Seligson, *Standard Methods of Clinical Chemistry*, vol. II, "Total Fatty Acids in Stool", 1958, Academic Press, pp. 34-39.
Stem et al., "A Comparison of the Efficacy and Tolerance of Pancrelipase and Placebo in the Treatment of Steatorrhea in Cystic Fibrosis Patients with Clinical Exocrine Pancreatic Insufficiency", *American Journal of Gasteroenterology*, 95(8):1932-1938 (2000).
Townes et al., "Amylase Polymorphism: Studies of Sera and Duodenal Aspirates in Normal Individuals and in Cystic Fibrosis", *American Journal of Human Genetics*, 28(4):378-389 (1976).
Veldee MS, Nutritional Assessment, Therapy, and Monitoring in Burtis CA, Ashwood ER (eds)., *Tietz Textbook of Clinical Chemistry*, 3rd Ed., 1999, W.B. Sanders Co, pp. 1385-1386.
"Pancreatin/Official Monographs", United States Pharmacopeia National Formulary, USP 24(19):1254-1255 (2000).
Chestukhina et al., "Crystal-forming proteins of Bacillis thuringiensis," Biochemistry Journal, 187:457-465 (1980).
Chernov et al., "Protein crystals and their growth," Journal of Structural Biology, 142:3-21 (2003).
Chung et al., "Cloning and nucleotide sequence of thermostable lipase gene from pseudomonas fluorescens SIK W1," Agricultural and Biological Chemistry, 55(9): 2359-2365 (1991).
Chung et al., "Overexpression of a thermostable lipase gene from pseudomonas fluorescens in Escherichia coli," Applied Microbiology and Biotechnology, 35:237-241 (1991).
Jaeger et al., "Bacterial Lipases," FEMS Microbiology Reviews, 15:23-63 (1994).
Lee et al., "Purification and characterization of pseudomonas fluorescens SIK W1 lipase expressed in Escherichia coli," Biochemica et Biophysica Acta, 1169:156-164 (1993).
Margolin et al., "Cross-linked enzyme crystals for lumenal therapies, "Proceed. Int'l Symp. Control. Rel. Bioact. Mater., 27:1012-13 (2000).
Matori et al., "Positional specificity of microbial lipases, "Journal of Fermentation and Bioengineering, 72(5):397-398 (1991).
Schmid et al., "Lipases: Interfacial Enzymes with attractive applications," Angew. Chem. Int. Ed., 37:1608-1633 (1998).
Sugiura, "Bacterial Lipases, "Lipases, edited by Bengt Borgstrom and Howard Brockman, 505-523 (1984).
Japanese Abstract 08-143469A, "Insufficiency of Exocrine Pancreas Treating Agent - Uses Lipase Active Over Wide PH Range, Derived from Microorganism," Amano Pharm KK, Jun. 4, 1996.
Beliaev, O.A., Eksp Klin Farmakol, 57(6), Nov-Dec., 1994, Abstract.
Boivin, et al. Are Diets Associated With Different Rates of Human Interdigestive and Postprandial Pancreatic Enzyme secretion?Gastroenterology 99:1763-1771 (1990).
Guarner et al., "Fate of oral enzymes in pancreatic insufficiency," Gut. 34:708-712 (1993).
Jain et al., "Effect of Ileal Perfusion of Carbohydrates and Amylase Inhibitor on Gastrointestinal Hormones and Emptying" Gastroenterology 96:377-387 (1989).
Pekarek, et al., "Double-walled polymer microspheres for controlled drug release" Nature 367:258-260 (1994).
Raimondo, et al. "Lipolytic Activity of Bacterial Lipase Survives Better Than That of Porcine Lipase in Human Gastric and Duodenal Content" Gastroenterology 107:231-235 (1994).
Roberts, "Enzyme Therapy for Malabsorption in Exocrine Pancreatic Insufficiency" Pancreas 4:496-503 (1989).
Suzuki, et al. "Bacterial Lipase and High-Fat Diets in Canine Exocrine Pancreatic Insufficiency: A new Therapy of Steatorrhea?" Gastroenterology 112:2048-2055 (1997).
Khalaf et al., "Cross-linked Enzyme Crystals as Highly Active Catalysts in Organic Solvents" J. Am. Chem. Soc. 118:5494-5495 (1996).
International Search Report and Written Opinion dated Sep. 27, 2001 from International Application No. PCT/US01/06074.

COMPOSITIONS AND METHODS FOR TREATING PANCREATIC INSUFFICIENCY

CROSS-REFERENCE TO RELATED APPLICATIONS

This application claims benefit under 35 U.S.C. §119(e) of U.S. provisional patent application Ser. No. 60/618,764, filed Oct. 14, 2004, the disclosure of which is herein incorporated by reference.

TECHNICAL FIELD OF THE INVENTION

The present invention relates to compositions for the treatment of conditions, including pancreatic insufficiency. The compositions of the present invention comprise lipase, protease and amylase in a particular ratio that provides beneficial results in patients, such as those afflicted with pancreatic insufficiency. This invention also relates to methods using such compositions for the treatment of pancreatic insufficiency.

BACKGROUND OF THE INVENTION

Digestion constitutes the physiological process by which ingested food is broken down into readily absorbed nutrient components. Following ingestion, food passes through various segments of the gastrointestinal tract and digestion is carried out, primarily by digestive enzymes. Three groups of digestive enzymes essential to this process include lipases (for fat digestion), proteases (for protein digestion) and amylases (for carbohydrate digestion).

Food digestion and nutrient absorption occur in the small intestine. There, ingested food is broken down by digestive enzymes for ready absorption. Most digestive enzymes are secreted by the pancreas and arrive in the small intestine through the pancreatic duct.

The pancreas effects a variety of exocrine and endocrine actions required for proper digestion, nutrition and metabolism. Pancreatic exocrine activities include the secretion of proteins that function as enzymes in the small intestine to catalyze the hydrolysis of fat into glycerol and fatty acids, protein into peptides and amino acids and carbohydrates into dextrins, disaccharides and monosaccharides, such as glucose. Exocrine pancreatic insufficiency (hereinafter "pancreatic insufficiency") results from a reduction in pancreatic function and can be caused by a number of clinical disorders. For example, pancreatic insufficiency is associated with cystic fibrosis, chronic pancreatitis, acute pancreatitis, pancreatic cancer and Shwachmann-Diamond Syndrome [E. P. DiMagno et al., in *The Pancreas: Biology, Pathobiology and Disease*, 2d Ed., V. Liang et al., eds., pp. 665-701 (1993)].

In patients afflicted with pancreatic insufficiency, the pancreas fails to produce and/or secrete sufficient amounts of digestive enzymes to support normal digestive processes, including digestion of fats, proteins and carbohydrates. As a result, those patients suffer from malabsorption of nutrients. Clinical manifestations of pancreatic insufficiency include abdominal cramping, bloating, diarrhea, steatorrhea, nausea and weight loss.

Pancreatic insufficiency is present in 89% of patients suffering from cystic fibrosis [D. Borowitz et al., "Use of Fecal Elastase-1 to Identify Misclassification of Functional Pancreatic Status in Patients with Cystic Fibrosis", *J. Pediatr.*, 145, pp. 322-326 (2004)]. Cystic fibrosis is an autosomal recessive genetic disorder that primarily affects the gastrointestinal and respiratory systems [S. M. Rowe et al., "Mechanisms of Disease: Cystic Fibrosis", *N. Engl. J. Med.*, 352, pp. 1992-2001 (1995)]. Abnormal amounts and viscosity of mucus produced in cystic fibrosis patients impede the secretion of sufficient amounts of pancreatic enzymes. The decreased volume of pancreatic secretions leads to inspissation within the pancreatic ducts, preventing egress of enzymes and bicarbonate into the duodenum. As a result, cystic fibrosis patients with pancreatic insufficiency suffer from impaired digestion and experience significant malabsorption of fat and protein. For example, such patients typically absorb less than 60% of dietary fat [M. Kraisinger et al., "Clinical Pharmacology of Pancreatic Enzymes in Patients with Cystic Fibrosis and in vitro Performance of Microencapsulated Formulations", *J. Clin. Pharmacol.*, 34, pp. 158-166 (1994)]. If left untreated, maldigestion and malabsorption in cystic fibrosis patients lead to malnutrition, inability to gain or maintain weight and decreased growth, as well as worsening of chronic suppurative lung disease [K. Gaskin et al., "Improved Respiratory Prognosis in CF Patients with Normal Fat Absorption", *J. Pediatr.*, 100, pp. 857-862 (1982); J. M. Littlewood et al., "Control of Malabsorption in Cystic Fibrosis", *Paediatr. Drugs*, 2, pp. 205-222 (2000)].

To date, standard therapy for pancreatic insufficiency is primarily based on orally-administered porcine pancrelipase, containing a mixture of lipases, trypsin, chymotrypsin, elastase and amylases. Although porcine pancreatic enzyme supplements contain substantial amounts of amylase, it has been reported that cystic fibrosis patients have normal amylase levels [P. L. Townes et al., "Amylase Polymorphism: Studies of Sera and Duodenal Aspirates in Normal Individuals and in Cystic Fibrosis", *Am. J. Hum. Genet.*, 28, pp. 378-389 (1976)]. Accordingly, it is believed that amylase serves no function in increasing polysaccharide digestion [E. Lebenthal et al., "Enzyme Therapy for Pancreatic Insufficiency: Present Status and Future Needs," *Pancreas*, 9, pp. 1-12 (1994)]. The lipase, protease and amylase components of porcine pancreatic supplements are typically present in a 1:3.5:3.5 ratio.

Pancreatic enzyme supplements are normally administered orally with meals. As these supplements pass through the low pH environment of the stomach, their enzyme activity diminishes rapidly. As a result, large quantities of enzyme concentrate (sometimes as many as 15 capsules or tablets per meal) have been required to ensure that sufficient active enzyme is present in the proximal intestine to relieve pancreatic insufficiency.

Because protease and lipase can become irreversibly inactivated in the stomach's acidic environment, enteric-coating technologies have been applied to pancrelipase products, to enclose enzymes in microbeads or otherwise treat them with a protective enteric coating. While such enteric-coatings improved the product profile, large quantities of supplements were still required to yield therapeutic benefit [J. H. Meyer, in *Pancreatic Enzymes in Health and Disease*, P. G. Lankisch, ed., pp. 71-88 (1991)]. A high-strength pancrelipase product line (Ultrase®) was introduced, with the goal of reducing the quantities of tablets or capsules necessary to treat pancreatic insufficiency. However, in 1991 the United States Cystic Fibrosis Foundation, in conjunction with the FDA, reported multiple cases of fibrosing colonopathy in children with cystic fibrosis taking such high-strength products [S. C. Fitzsimmons et al., "High-Dose Pancreatic-Enzyme Supplements and Fibrosing Colonopathy in Children with Cystic Fibrosis", *N. Engl. J. Med.*, 336, pp. 1283-1289 (1997)]. In these patients, colonic fibrosis caused strictures that often required surgery and, in some cases, colectomy.

As a means toward reducing daily doses of pancreatic enzymes, the FDA removed the high strength products (defined as greater than 2,500 USP units per kg body weight) from the market [D. S. Borowitz et al., "Use of Pancreatic Enzyme Supplements for Patients with Cystic Fibrosis in the Context of Fibrosing Colonopathy", *J. Pediatr.,* 127, pp. 681-684 (1995)]. In addition, the United States Cystic Fibrosis Foundation, jointly with the FDA, recommended a detailed examination of the complex nature of porcine enzyme extracts [Id.]. The Consensus Panel also recommended investigation of alternative, acid-stable lipases.

Whether or not a given pancreatic enzyme supplement is enterically-coated, the bioavailability of such supplements varies widely, due to differentials in acidification of the intestine among patients. As a result, many patients take pH altering drugs, such as histamine-2 ($H_2$) receptor blockers and proton pump inhibitors (PPI), to improve the clinical efficacy of the enzyme supplements [P. G. Lankish, "Enzyme Treatment of Exocrine Pancreatic Insufficiency in Chronic Pancreatitis', *Digestion,* 54 (Supp. 2), pp. 21-29 (1993); D. Y. Graham, "Pancreatic Enzyme Replacement: the Effect of Antacids or Cimetidine", *Dig. Dis. Sci.,* 27, pp. 485-490 (1982); J. H. Saunders et al., "Inhibition of Gastric Secretion in Treatment of Pancreatic Insufficiency", *Br. Med. J.,* 1, pp. 418-419 (1977); H. G. Heijerman et al., "Omeprazole Enhances the Efficacy of Pancreatin (Pancrease) in Cystic Fibrosis", *Ann. Inter. Med.,* 114, pp. 200-201 (1991); M. J. Bruno et al., "Comparative Effects of Adjuvant Cimetidine and Omprazole during Pancreatic Enzyme Replacement Therapy", *Dig. Dis. Sci.,* 39, pp. 988-992 (1994)].

Variability in terms of potency and pharmaceutical properties and lack of stability have also been identified as important factors contributing to a poor response of some patients to conventional pancreatic enzyme supplements [C. L. Chase et al., "Enzyme Content and Acid Stability of Enteric-Coated Pancreatic Enzyme Products in vitro", *Pancreas,* 30, pp. 180-183 (2005); D. S. Borowitz et al., *J. Pediatr.,* 127, supra; C. J. Powell et al., "Colonic Toxicity from Pancreatins: a Contemporary Safety Issue", *Lancet,* 353, pp. 911-915 (1999); E. Lebenthal et al., "Enzyme Therapy for Pancreatic Insufficiency: Present Status and Future Needs", *Pancreas,* 9, pp. 1-12 (1994); P. Regan et al., "Comparative Effects of Antacids, Cimetidine and Enteric Coating on the Therapeutic Response to Oral Enzymes in Severe Pancreatic Insufficiency", *N. Eng. J. Med.,* 297, pp. 854-858 (1977)]. These include batch-to-batch variation in enzyme activity, susceptibility to loss of activity over time by exposure to sunlight, heat or humidity and a poorly defined profile of adverse reactions [D. S. Borowitz et al., *J. Pediatr.,* 127, supra]. Other factors that complicate pancreatic insufficiency therapy include destruction of the replacement enzymes by gastric juice and/or intraluminal proteases, asynchronous gastric emptying of enzyme supplement and meal nutrients, and delayed liberation of enzyme from enteric-coated preparations [P. G. Lankish, *Digestion,* 54 supra; P. Regan et al., *N. Eng. J. Med.,* 297, supra].

Due to the problems of potency, stability and bioavailability characterizing conventional pancreatic enzyme supplements, the use of microbially-derived enzymes as alternatives to porcine-derived enzymes has been proposed. For example, U.S. Pat. No. 6,051,220 describes compositions comprising one or more acid stable lipases and one or more acid stable amylases, both preferably of fungal origin. United States patent application 2004/0057944 describes compositions comprising *Rhizopus delemar* lipase, *Aspergillus melleus* protease and *Aspergillus oryzae* amylase. United States patent application 2001/0046493 describes compositions comprising crosslinked crystalline bacterial lipase, together with a fungal or plant protease and a fungal or bacterial amylase.

Despite such developments, the need still exists for optimizing dosage formulations to further improve both the efficacy of pancreatic enzyme supplements and patient compliance. The goal of a pancreatic enzyme supplement displaying the highest efficacy at the lowest dose, and characterized by a well-defined safety profile, remains of great importance to all patients suffering from pancreatic insufficiency, including those in the cystic fibrosis community.

SUMMARY OF THE INVENTION

The present invention is directed to compositions and methods for treating conditions, including pancreatic insufficiency. According to a preferred embodiment, the compositions of this invention are characterized by crosslinked microbial lipase crystals, microbial protease and microbial amylase, in a ratio of about 1.0:1.0:0.15 USP units of enzyme activity. Advantageously, these compositions are characterized by stable enzyme components, in turn ensuring in vivo delivery of active enzyme to the gastrointestinal tract and thereby allowing effective low dose treatment regimens for pancreatic insufficiency.

DETAILED DESCRIPTION OF THE INVENTION

Figure 1:
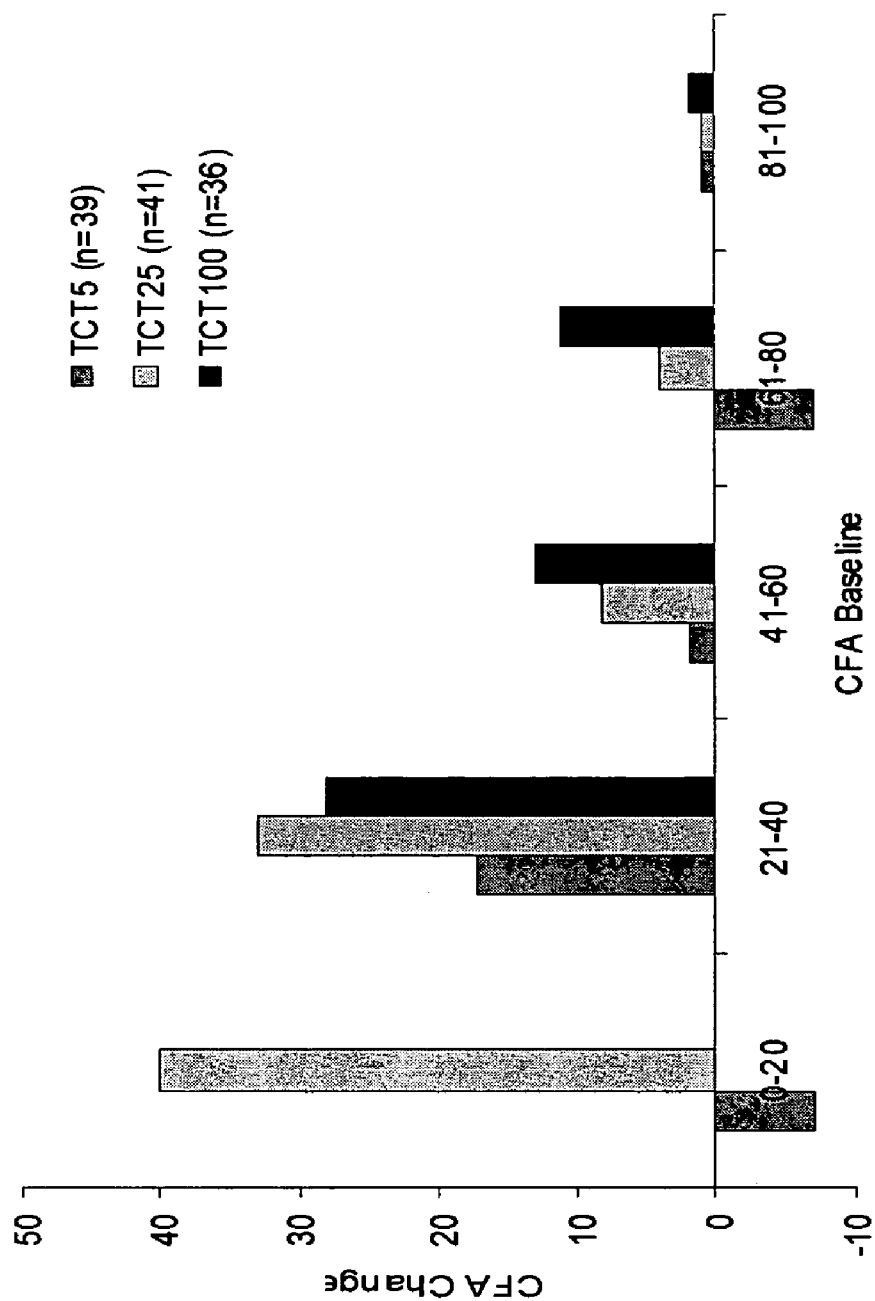
FIG. 1 illustrates the change in mean coefficient of fat absorption ("CFA"), as compared to baseline, in patients treated with compositions according to the present invention during a Phase 2 study.

The present invention relates to the discovery that compositions comprising lipase, protease and amylase, in a ratio of about 1.0:1.0:0.15 USP units of enzyme activity, are effective for treating conditions, including pancreatic insufficiency. The unique ratio of lipase to protease to amylase allows treatment of those conditions in low dose therapy regimens not possible with conventional porcine derived pancreatic enzyme supplements. Further, this lipase to protease to amylase ratio avoids a high concentration of protease which, in conventional enzyme supplements, has been thought to be responsible for fibrosing colonopathy [D. S. Borowitz et al., *J. Pediatr.*, 127, supra].

According to a preferred embodiment, the compositions of this invention comprise crosslinked microbial lipase crystals, a microbial protease and a microbial amylase in a ratio of about 1.0:1.0:0.15 USP units of enzyme activity.

Definitions

The following terms, unless otherwise indicated, shall be understood to have the following meanings:

The term "amorphous" refers to any state other than the crystal, crystalline or semi-crystalline state. Amorphous matter includes amorphous solids and liquids.

The term "crystal" or "crystalline" refers to one form of the solid state matter comprising atoms arranged in a pattern that repeats periodically in three dimensions [see, e.g., Barrett, *Structure of Methals*, 2$^{nd}$ ed., (1952)]. The crystal or crystalline form of an enzyme is distinct from the amorphous or semi-crystalline forms thereof. Crystals display characteristic features, including a lattice structure, characteristic shapes and optical properties, such as, e.g., refractive index.

The term "semi-crystalline" refers to a solid state of matter having both crystalline and amorphous regions.

The term "subject", "patient" or "individual" refers to any mammal, including any animal classified as such, including humans and other primates.

The term "maldigestion" refers to the impaired breakdown of nutrients (such as fats, proteins and carbohydrates) into their absorbable constituents (mono-, di-, or oligosaccharides, amino acids, oligopeptides, fatty acids and monoglycerides). Maldigestion may result from several conditions, including pancreatic insufficiency.

The term "malabsorption" refers to the impaired absorption of digested nutrients, including vitamins and trace elements, from the small intestine or large bowel. Malabsorption may be due to defective mucosal uptake by the intestinal lining or particular abnormalities of digestion. Intestinal malabsorption may occur for many nutrients, or for specific macronutrients, namely fats, proteins or carbohydrates, as well as for micronutrients, such as calcium, magnesium, iron and vitamins. Malabsorption may result from several conditions, including pancreatic insufficiency. Protein malabsorption is referred to as "azotorrhea". Lipid malabsorption is referred to as "steatorrhea".

The term "lipase" refers to an enzyme that catalyzes the hydrolysis, (i.e., separating the hydroxyl group and the hydrogen atom of compounds into fragments by the addition of water) of lipids to glycerol and simple fatty acids. This enzymatic reaction usually requires calcium ions ($Ca^{2+}$). Lipases secreted by the pancreas are extremely important for the digestion of fat (triglycerides) in the upper loop of the small intestine. According to a preferred embodiment, the lipases useful in the compositions and methods of this invention are non-pancreatic lipases, i.e., they are not purified from human or animal pancreatic tissue. According to a more preferred embodiment of the present invention, the lipases are microbial lipases. According to a further preferred embodiment of this invention, the lipase is a bacterial lipase. Bacterial lipases include, for example, *Pseudomonas* lipase and/or *Burkholderia* lipase.

Microbial lipases may be isolated from their native microbial source, or they may be recombinant microbial lipases produced via recombinant DNA technology by a suitable host cell, selected from any one of bacteria, yeast, fungi, plant, insect or mammalian host cells in culture, preferably bacteria. Recombinant lipases encompass or are encoded by nucleic acids from a naturally occurring lipase sequence. Further, recombinant lipases include an amino acid sequence that is homologous or substantially identical to a naturally occurring sequence, as well as those lipases encoded by a nucleic acid that is homologous or substantially identical to a naturally occurring lipase-encoding nucleic acid. Alternatively, lipases useful in the compositions and methods of this invention may be synthesized by conventional peptide synthesis techniques.

The term "protease" refers to a proteinase, proteolytic enzyme or peptidase, which is an enzyme that catalyzes the splitting of interior amide peptide bonds in a protein. Specifically, proteases catalyze the conversion of proteins into their component amino acids by cleaving the amide linkage between the carboxyl group of one amino acid and the amino group of another. Proteases are generally identified by their catalytic type, e.g., aspartic acid peptidases, cysteine (thiol) peptidases, metallopeptidases, serine peptidases, threonine peptidases, alkaline or semi-alkaline proteases, neutral and peptidases of unknown catalytic mechanism (see http://merops.sanger.ac.uk). According to a preferred embodiment, the proteases useful in the compositions and methods of this invention are non-pancreatic proteases, i.e., they are not purified from human or animal pancreatic tissue. According to a more preferred embodiment of the present invention, the proteases are microbial proteases. According to a further preferred embodiment of this invention, the protease is a fungal protease. According to one further embodiment of this invention, the protease is *Aspergillus melleus* protease.

Microbial proteases may be isolated from their native microbial source or they may be recombinant microbial proteases produced via recombinant DNA technology by a suitable host cell, selected from any one of bacteria, yeast, fungi, plant, insect or mammalian host cells in culture, preferably fungi. Recombinant proteases encompass or are encoded by nucleic acids from a naturally occurring protease sequence. Further, recombinant proteases include an amino acid sequence that is homologous or substantially identical to a naturally occurring sequence, as well as those proteases encoded by a nucleic acid that is homologous or substantially identical to a naturally occurring protease-encoding nucleic acid. Alternatively, proteases useful in the compositions and methods of this invention may be synthesized by conventional peptide synthesis techniques.

The term "amylase" refers to an enzyme that is produced in the pancreas and also in the salivary glands in humans but not all mammals. Human salivary amylase is known as ptyalin. Amylase is the main digestive enzyme responsible for digesting carbohydrates, e.g., polysaccharides, by catalyzing the conversion of the two components of starch (amylose and amylo-pectin) into simple sugars in the small intestine. More specifically, amylase hydrolyzes starch, glycogen and dextrin to form glucose, maltose and the limit-dextrins. Clinically, blood amylase levels are often elevated in conditions of acute and sometimes chronic pancreatitis. The term "non-pancreatic amylases" refers to amylases which are not purified from human or animal pancreatic tissue. According to a more preferred embodiment of the present invention, the amylases are microbial amylases. According to a further preferred embodiment of this invention, the amylase is a fungal amylase.

According to one further embodiment of this invention, the amylase is *Aspergillus* amylase and, preferably, is *Aspergillus oryzae* amylase.

Microbial amylases may be isolated from their native microbial source or they may be recombinant microbial amylases produced via recombinant DNA technology by a suitable host cell, selected from any one of bacteria, yeast, fungi, plant, insect or mammalian host cells in culture, preferably fungi. Recombinant amylases encompass or are encoded by nucleic acids from a naturally occurring amylase sequence. Further, recombinant amylases include an amino acid sequence that is homologous or substantially identical to a naturally occurring sequence, as well as those amylases encoded by a nucleic acid that is homologous or substantially identical to a naturally occurring amylase-encoding nucleic acid. Alternatively, amylases useful in the compositions and methods of this invention may be synthesized by conventional peptide synthesis techniques.

The terms "therapeutically effective dose" or "therapeutically effective amount" refer to that amount of a composition that results in prevention, delay or onset of symptoms, or amelioration of symptoms of the condition to be treated. A therapeutically effective amount is that sufficient to treat, prevent, reduce the severity, delay the onset, or reduce the occurrence of one or more symptoms of the condition to be treated. Conditions that may be treated using the compositions of this invention include, for example, pancreatic insufficiency, malabsorption, and maldigestion.

The term "USP Unit" refers to the United States Pharmacopoeia unit of enzyme activity present in an agent or composition. One USP Unit of lipase, protease or amylase is defined in *Pancrelipase*, USP, U.S. Pharmacopeia National Formulary, USP 24, pp. 1254-1255 (2000). Assays for lipase, protease and amylase are disclosed in that reference and are incorporated herein by reference.

Characteristics of the Compositions of this Invention

Advantageously, the compositions of the present invention improve the absorption of fat, protein and starch in patients suffering from conditions such as, for example, pancreatic insufficiency, leading to improved nutrition and growth. The compositions retain high levels of specific activity in an acid-pepsin environment. Such is the case because their enzyme components withstand the acidic environment of the upper gastrointestinal tract, including the low pH of the stomach and the high protease levels of the gastrointestinal tract; allowing the enzymes to be delivered to the intestine in active form. As a result, they can be administered in lower amounts per dose and by means of fewer administrations, as compared with porcine pancreatic enzyme supplements. This, in turn, accommodates improved patient compliance.

Furthermore, the compositions of the present invention may be administered to a subject without the need for enteric coatings or addition of acid-suppressing agents. Such is the case because the microbial derived enzyme components used in various embodiments of the compositions of this invention are more stable toward stomach acid than porcine pancreatic enzymes.

The Lipase Component

The lipase component of the compositions of the present invention is preferably a microbial lipase. More preferably, the lipase is bacterial, rather than fungal or of plant origin.

The lipase is preferably one that is stable in an acidic pH environment and/or that is resistant to proteolytic degradation. The lipase may also be employed in a form that renders enhances its stability to acidic pH and/or its resistance to proteolytic degradation. To that end, the lipase is preferably in the form of crosslinked crystals. Any of the above-described lipases may be used to form a crosslinked lipase crystal component of the compositions of the present invention.

Crystallization of the Lipase

Lipase crystals useful in the compositions of the present invention may be grown using conventional methods, such as batch crystallization. See, for example, U.S. Pat. No. 6,541,606. Alternatively, lipase crystals may be grown by controlled precipitation of protein out of an aqueous solution, or an aqueous solution containing organic solvents. See, for example, U.S. Pat. No. 5,618,710 and United States patent application 2003/0017144. As will be appreciated by those of skill in the art, conditions to be controlled during crystallization include the rate of evaporation of solvent, the presence of appropriate co-solutes and buffers, pH and temperature, for example.

Lipase crystals may be produced by combining the lipase enzyme to be crystallized with an appropriate solvent or aqueous solvent containing appropriate precipitating agents, such as salts or organic agents. The solvent is combined with the lipase and optionally subjected to agitation at a temperature determined experimentally to be appropriate for induction of crystallization and acceptable for maintenance of protein stability and activity. The solvent can optionally include co-solutes, such as divalent cations, co-factors or chaotropes, as well as buffer species to control pH. The need for and concentrations of co-solutes may be determined experimentally to facilitate crystallization. For an industrial scale process, the controlled precipitation leading to crystallization may best be carried out by the simple combination of protein, precipitant, co-solutes, and, optionally, buffers in a batch process. Alternatively, laboratory crystallization methods, such as dialysis or vapor diffusion may also be used. McPherson et al., *Methods Enzymol.*, 114, pp. 112-120 (1985) and Gilliland, *J. Crystal Growth*, 90, pp. 51-59 (1988) include a comprehensive list of suitable conditions in the crystallization literature. Occasionally, incompatibility between the crystallization medium and the crosslinker may require changing the buffer or solvent prior to crosslinking.

Lipase crystallizes under a number of conditions, including a pH range of about 4-9. For preparation of the lipase component of the compositions of the present invention, useful precipitants include isopropanol, Tert-butanol, 2-methyl-2,4-pentandiol (MPD), ammonia sulfate, sodium chloride, magnesium chloride and others known to those skilled in the art. Useful salts include divalent or monovalent cations and their salts.

Lipase crystals useful in the compositions of this invention may have a longest dimension between about 0.01 μm and about 500 μm, alternatively between about 0.1 μm and about 50 μm, or between about 0.1 μm and about 10 μm. They may be of a shape selected from the group consisting of spheres, needles, rods, plates, such as hexagons and squares, rhomboids, cubes, bipyramids and prisms.

Crosslinking of the Lipase Crystals

Once lipase crystals have been grown in a suitable medium, they may be crosslinked. Crosslinking results in stabilization of the crystal lattice by introducing covalent links between the constituent protein molecules of the crystal. This makes possible the transfer of the enzyme into an alternate environment that, for a given enzyme, might otherwise be incompatible with the existence of the crystal lattice or the intact enzyme.

As a result of crosslinking of the lipase crystals, the enzymatic stability (e.g., pH, temperature, mechanical and/or chemical stability), the pH profile of lipase activity, the solubility, the uniformity of crystal size or volume, the rate of release of lipase from the crystal, and/or the pore size and shape between individual enzyme molecules in the underlying crystal lattice may be altered.

Advantageously, crosslinking is carried out in such a way that the resulting crosslinked crystals comprise a lipase that displays at least about 10%, 20%, 30%, 40%, 50%, 60%, 70%, 80%, 90%, 95%, 96% 97%, 98%, 99%, 99.5%, 99.7%, or 99.9% or more of lipase activity as compared to unmodified lipase. Stability may be increased by at least about 20%, 30%, 40%, 50%, 60%, 70%, 80%, 90%, 100%, 150%, 200%, 250%, 300% or more, as compared to unmodified lipase. Stability can be measured under conditions of storage, such as pH stability, temperature stability, stability against proteases, including gastrointestinal proteases and Pronase™, dissolution stability or as in vivo biological stability, for example.

In certain instances, crosslinking of the lipase crystals slows the dissolution of the lipase into solution, effectively immobilizing the enzyme molecules into microcrystalline particles. Upon exposure to a trigger in the environment surrounding the crosslinked lipase crystals, such as conditions of use rather than storage, the lipase crystals dissolve, releasing lipase polypeptide and/or increasing lipase activity. The rate of dissolution may be controlled by one or more of the following factors: the degree of crosslinking, the length of time of exposure of lipase crystals to the crosslinking agent, the rate of addition of the crosslinking agent to the lipase crystals, the nature of the crosslinker, the chain length of the crosslinker, pH, temperature, presence of sulfahydryl reagents, such as cysteine or gluthathione, the surface area of the crosslinked lipase crystals, the size of the crosslinked lipase crystals or the shape of the crosslinked lipase crystals, for example.

The lipase crystals may be crosslinked using one or a combination of crosslinking agents, including multifunctional crosslinking agents, including bifunctional reagents, at the same time (in parallel) or in sequence. In various embodiments, the crosslinks between the lipase crystals lessen or weaken upon exposure to a trigger in the surrounding environment, or over a given period of time; thus leading to lipase dissolution or release of activity. Alternatively, the crosslinks may break at the point of attachment, leading to protein dissolution or release of activity. See, for example, U.S. Pat. Nos. 5,976,529 and 6,140,475. Crosslinking may be carried out according to any conventional crosslinking technique.

The final concentration of crosslinker in the crosslinked lipase crystals should range between about 0.001 mM and about 300 mM, preferably between about 1.0 mM and about 50 mM, most preferably between about 2.0 mM and about 5.0 mM.

According to a preferred embodiment of this invention, the crosslinking agent is bis(sulfosuccini-midyl) suberate ("BS$^3$"). Other useful crosslinkers include glutaraldehyde, succinaldehyde, octane-dialdehyde and glyoxal. Additional multifunctional crosslinkers agents include halo-triazines, e.g., cyanuric chloride; halo-pyrimidines, e.g., 2,4,6-trichloro/bromo-pyrimidine; anhydrides or halides of aliphatic or aromatic mono- or di-carboxylic acids, e.g., maleic anhydride, (meth)acryloyl chloride, chloroacetyl chloride; N-methylol compounds, e.g., N-methylol-chloro acetamide; di-isocyanates or di-isothiocyanates, e.g., phenylene-1,4-di-isocyanate and aziridines. Other crosslinkers include epoxides, such as, for example, di-epoxides, tri-epoxides and tetra-epoxides. For a representative listing of other available crosslinkers see, for example, the 2003-2004 edition of the Pierce Chemical Company Catalog. Other examples of crosslinkers include: dimethyl 3,3'-dithiobispropionimidate. HCl (DTBP); dithiobis (succinimidylpropionate) (DSP); bismaleimidohexane (BMH); 1,5-difluoro-2,4-dinitrobenzene (DFDNB); dimethylsuberimidate.2HCl (DMS); disuccinimidyl glutarate (DSG); disulfosuccinimidyl tartarate (Sulfo-DST); 1-ethyl-3-[3-dimethylaminoproplyl]carbodiimide hydrochloride (EDC); ethylene glycolbis [sulfo-succinimidylsuccinate] (Sulfo-EGS); N-[γ-maleimido-butyryloxy]succinimide ester (GMBS); N-hydroxysulfo-succinimidyl-4-azidobenzoate (Sulfo-HSAB); sulfo-succinimidyl-6-[α-methyl-α-(2-pyridyldithio)toluamido] hexanoate (Sulfo-LC-SMPT); bis-[β-(4-azido-salicylamido) ethyl]disulfide (BASED); and NHS-PEG-Vinylsulfone (NHS-PEG-VS).

Reversible crosslinkers may also be used. Such reversible crosslinkers are multifunctional crosslinkers into which a trigger is incorporated as a separate group. The reactive functionality is involved in linking together reactive amino acid side chains in a protein and the trigger consists of a bond that can be broken by altering one or more conditions in the surrounding environment (e.g., pH, presence of reducing agent, temperature or thermodynamic water activity).

The crosslinker may be homofunctional or heterofunctional. The reactive functionality (or moiety) may, e.g., be chosen from one of the following functional groups (where R, R', R" and R'" may be alkyl, aryl or hydrogen groups):

I. Reactive acyl donors, such as, e.g.: carboxylate esters RCOOR', amides RCONHR', Acyl azides RCON$_3$, carbodiimides R—N=C=N—R', N-hydroxyimide esters, RCO—O—NR', imidoesters R—C=NH2$^+$ (OR'), anhydrides RCO—C—COR', carbonates RO—CO—O—R', urethanes RNHCONHR', Acid halides RCOHal (where Hal=a halogen), acyl hydrazides RCONNR"R", and O-acylisoureas RCO—O—C=NR'(—NR"R'").

II. Reactive carbonyl groups, such as, e.g.: alehydes RCHO and ketones RCOR', acetals RCO(H$_2$)R', and ketals RR'CO$_2$R'R" (reactive carbonyl containing functional groups known to those skilled in the art of protein immobilization and crosslinking (Pierce Catalog and Handbook, Pierce Chemical Company 2003-2004; S. S. Wong, *Chemistry of Protein Conjugation and Crosslinking*, (1991).

III. Alkyl or aryl donors, such as, e.g.: alkyl or aryl halides R-Hal, azides R—N$_3$, sulfate esters RSO$_3$R', phosphate esters RPO(OR'$_3$), alkyloxonium salts R$_3$O$^+$, sulfonium R$_3$S$^+$, nitrate esters RONO$_2$, Michael acceptors RCR'=CR'"COR", aryl fluorides ArF, isonitriles RN$^+$=C—, haloamines R$_2$N-Hal, alkenes and alkynes.

IV. Sulfur containing groups, such as, e.g.: Disulfides RSSR', sulfhydryls RSH, and epoxides R$_2$COCR'$_2$.

V. Salts, such as, e.g.: alkyl or aryl Ammonium salts R$_4$N$^+$, carboxylate RCOO—, Sulfate ROSO$_3$—, phosphate ROPO$_3$", and amines R$_3$N.

Reversible crosslinkers, for example, comprise a trigger. A trigger includes an alkyl, aryl, or other chain with activating group that can react with the protein to be crosslinked. Those reactive groups can be of a variety of groups, such as those susceptible to nucleophilic, free radical or electrophilic displacement, including halides, aldehydes, carbonates, urethanes, xanthanes and epoxides, among others. For example, reactive groups may be labile to acid, base, fluoride, enzyme, reduction, oxidation, thiol, metal, photolysis, radical or heat.

The crosslinked lipase crystal may be provided in powder form by, for example, lyophilization or spray-drying. Lyophilization, or freeze drying, allows water to be separated from the composition, producing a crystal that can be stored at non-refrigerated (room) temperature for extended periods of time and then easily reconstituted in aqueous, organic, or mixed aqueous-organic solvents of choice, without the formation of amorphous suspensions and with a minimal risk of denaturation. Carpenter et al., *Pharm. Res.*, 14, pp. 969-975 (1997). Lyophilization may be carried out as described in U.S. Pat. No. 5,618,710, or by any other method known in the art. For example, the crosslinked lipase crystal is first frozen and then placed in a high vacuum where the crystalline water sublimes, leaving behind a lipase crystal containing only the tightly bound water molecules.

Characteristics of the Crosslinked Lipase Crystals

The enzymatic activity of the crosslinked lipase crystals may be measured using any conventional method. For example, lipase activity may be determined spectrophotometrically as described in Example 6 of U.S. Pat. No. 5,618,710. Lipase activity may be assessed by monitoring hydrolysis of the substrate p-nitrophenyl acetate. Substrate cleavage is monitored by increasing absorbance at 400 nm, with an initial substrate concentration of 0.005% and a starting enzyme concentration of $1.5 \times 10^{-8}$ M. Lipase enzyme is added to a 5 ml reaction volume containing substrate in 0.2 M Tris pH 7.0 at room temperature. Crystalline lipase is removed from the reaction mixture by centrifugation prior to measuring absorbance.

Alternatively, lipase activity may be measured in vitro by hydrolysis of olive oil, as described in Examples 2-4 of U.S. Pat. No. 5,614,189.

Lipase activity can also be measured in vivo. For example, a small volume (about 3 ml) of olive oil or corn oil can be labeled with $^{99}$Tc—(V) thiocyanate, and crystalline lipase can be labeled with $^{111}$In. The labelled fat is mixed with an animal food onto which the labelled crystalline lipase has been sprinkled. Scintigraphic images of the proximal and distal stomach and small intestine are obtained until <5% of the activity remains in the stomach. Emptying curves for each of the isotopes (e.g., percent retention in the stomach over time) and amounts of isotopes entering the proximal, middle and distal small bowel from the respective regions of interest are then determined.

Preferably, the crosslinked lipase component of the compositions of the present invention has a high specific activity. A high specific activity lipase activity is typically one that shows a specific activity to triolein (olive oil) at greater than 500, 1,000, 4,000, 5,000, 6,000, 7,000, 8,000, 9,000 or more units/mg protein.

Preferably, the crosslinked lipase component of the compositions of the present invention is also stable for an extended period of time in a harsh environment found in the gastrointestinal regions, i.e., gastric, duodenal and intestinal regions. For example, the lipase is preferably stable for at least one hour in acidic pH, e.g., an environment in which the pH is less than 7, 6, 5, 4.5, 4, 3.5, 3, 2.5, 2, 1.5 or less. As used herein, "stable" means that the lipase crystal is more active than the soluble form of the lipase for a given condition and time. Thus, a stable lipase crystal retains a higher percentage of its initial activity than the corresponding soluble form of the lipase. In some embodiments, the lipase crystal retains at least 10% of its activity after exposure to the given conditions and time. In other embodiments, the lipase retains at least 20%, 30%, 40%, 50%, 60%, 70%, 80%, 90% or more of its activity.

Alternatively, or in addition, the crosslinked lipase crystal component of the compositions of this invention is heat resistant. For example, in various embodiments, it is stable for at least one hour at 30° C., 37° C. or 40° C.

The Protease Component

The protease component of the compositions of the present invention is a microbial protease. Preferably, the protease is of fungal, rather than bacterial or plant origin. More preferably, the protease is an *Aspergillus* protease. Most preferably, the protease is *Aspergillus melleus* protease. According to a preferred embodiment, the protease component of the compositions of the present invention is in crystallized, non-crosslinked form. Protease crystals may be prepared according to the crystallization techniques described above for lipase, using, for example, ethanol as a precipitant. Alternatively, the protease component of the compositions of this invention may be in non-crystalline forms, in crosslinked crystalline forms, or coated, or encapsulated or otherwise formulated so that it does not digest the other protein components of the compositions.

The Amylase Component

The amylase component of the compositions of the present invention is a microbial amylase. Preferably, the amylase is of fungal, rather than bacterial or plant origin. More preferably, the amylase is an *Aspergillus* amylase. Most preferably, the amylase is *Aspergillus oryzae*. According to a preferred embodiment, the amylase component of the compositions of the present invention is in amorphous form. Alternatively, the amylase component of the compositions of this invention may be in crystalline forms, including crosslinked and non-crystalline forms, or coated, or encapsulated or otherwise formulated so that it retains its activity after oral administration.

Compositions Comprising Crosslinked Lipase Crystals, a Protease and an Amylase

The compositions according to the present invention include those comprising crosslinked microbial lipase crystals, a microbial protease and a microbial amylase, in a ratio of about 1.0:1.0:0.15 USP units of enzyme activity, together with one or more excipients. Preferably, the lipase is a bacterial lipase and the protease and amylase are of fungal origin. Most preferably, the composition comprises bacterial lipase crystals crosslinked with BS-3 crosslinker, *Aspergillus melleus* protease crystals and soluble *Aspergillus oryzae* amylase; in a ratio of about 1.0:1.0:0.15 USP units of enzyme activity.

The crosslinking of the lipase component of the compositions of this invention provides added stability at pH extremes and protection under proteolysis, while the protease and amylase components maintain maximum solubility for effective dissolution. More particularly, the crystallization and crosslinking of the lipase component helps provide a composition with enhanced enzyme activity at lower dosages. The crystal form of the protease also helps to provide enhanced enzyme stability, purity and potency.

In alternate embodiments of the present invention, the lipase may be in any stabilized form, and either or both of the protease and amylase components of the compositions may be in crystal, amorphous or semi-crystalline form. Alternatively, either or both may be in lyophilized form. And, regardless of their form, either or both may be crosslinked.

The compositions of the present invention advantageously lead to correlated increases in the coefficient in fat absorption and the coefficient of nitrogen absorption in patients treated with them. In addition, the compositions of this invention include a level of amylase that provides increased starch digestion and carbohydrate absorption in those patients. By virtue of the present invention, it has been discovered that such an effect on starch digestion and carbohydrate absorption may be achieved using far less amounts of amylase in relation to lipase and protease than those of porcine pancreatic supplements. This discovery is contrary to belief in the art that amylase is not necessary for the treatment of pancreatic insufficiency, particularly in cystic fibrosis patients.

The excipients useful in the compositions according to this invention act as a filler or a combination of fillers, such as those used in pharmaceutical compositions. In a preferred embodiment of this invention, the excipient comprises microcrystalline cellulose, Maltrin, Crospovidone, colloidal silcon dioxide, magnesium stearate and talc. A further preferred group of excipients includes one, or a mixture of: sucrose, trehalose, lactose, sorbitol, lactitol, mannitol, inositol, salts of sodium and potassium, such as acetate, phosphates, citrates and borate, glycine, arginine, polyethylene oxide, polyvinyl alcohol, polyethylene glycol, hexylene glycol, methoxy polyethylene glycol, gelatin, hydroxypropyl-β-cyclodextrin, polylysine and polyarginine.

Other preferred excipients may be any one, or a mixture of: either 1) amino acids, such as glycine, arginine, aspartic acid, glutamic acid, lysine, asparagine, glutamine, proline; 2) carbohydrates, e.g., monosaccharides such as glucose, fructose, galactose, mannose, arabinose, xylose, ribose; 3) disaccharides, such as lactose, trehalose, maltose, sucrose; 4) polysaccharides, such as maltodextrins, dextrans, starch, glycogen; 5) alditols, such as mannitol, xylitol, lactitol, sorbitol; 6) glucuronic acid, galacturonic acid; 7) cyclodextrins, such as methyl cyclodextrin, hydroxypropyl-β-cyclodextrin and alike; 8) inorganic molecules, such as sodium chloride, potassium chloride, magnesium chloride, phosphates of sodium and potassium, boric acid, ammonium carbonate and ammonium phosphate; 9) organic molecules, such as acetates, citrate, ascorbate, lactate; 10) emulsifying or solubilizing/stabilizing agents like acacia, diethanolamine, glyceryl monostearate, lecithin, monoethanolamine, oleic acid, oleyl alcohol, poloxamer, polysorbates, sodium lauryl sulfate, stearic acid, sorbitan monolaurate, sorbitan monostearate, and other sorbitan derivatives, polyoxyl derivatives, wax, polyoxyethylene derivatives, sorbitan derivatives; and 11) viscosity increasing reagents like, agar, alginic acid and its salts, guar gum, pectin, polyvinyl alcohol, polyethylene oxide, cellulose and its derivatives propylene carbonate, polyethylene glycol, hexylene glycol, tyloxapol. Salts of such compounds may also be used.

Additional examples of excipients are described in the *Handbook of Pharmaceutical Excipients*, published jointly by the American Pharmaceutical Association and the Pharmaceutical Society of Great Britain. With respect to the compositions, according to this invention, excipients are inactive ingredients, and lipase, protease and amylase are active ingredients. The ratio of active to inactive ingredients in the compositions of this invention, on a w/w basis, may between about 1:9 to about 9:1, preferably between about 1:6 to about 6:1.

In an alternate embodiment of this invention, any one of the lipase, protease or amylase components may be present in the composition in association with a polymeric carrier. This provides an acid-resistant controlled release composition that allows enzyme delivery in effective amounts and low dosages to the intestine, i.e., the distal bowel, following oral ingestion.

Useful polymeric carriers include, for example, polymers used for encapsulation of protein crystals for delivery of proteins, including controlled release biological delivery. Such polymers include biocompatible and biodegradable polymers, or mixtures thereof. Preferably, the polymeric carrier is a biodegradable polymer. The rate of dissolution and, therefore, delivery of enzymes will be determined by the particular encapsulation technique, polymer composition, polymer crosslinking, polymer thickness, polymer stability, enzyme crystal geometry and degree, if any, of enzyme crosslinking. According to one embodiment, the compositions of this invention are encapsulated within a matrix of the polymeric carrier; thus providing further protection for the lipase, protease and amylase components from the harsh environment of the gastrointestinal tract.

Composition Dosage Routes, Forms, Regimens and Methods for Treatment

According to a preferred embodiment, the compositions of this invention are useful in methods for treating pancreatic insufficiency in any subject, including those suffering from cystic fibrosis. According to an alternative embodiment, the compositions of this invention are useful in methods for treating malabsorption in a subject. Further embodiments of this invention include use of the compositions of this invention for increasing the coefficient of fat absorption, or for increasing the coefficient of nitrogen absorption in a subject. Another embodiment of this invention includes use of those compositions to increase both the coefficient of fat absorption and the coefficient of nitrogen absorption in a subject, optionally by the same amount. In a further embodiment, the compositions of this invention are useful in methods for increasing carbohydrate absorption in a subject.

The methods for treatment using the compositions according to this invention comprise the step of administering to a subject a therapeutically effective amount of such a composition. Any of the methods of this invention may be used to treat any subject suffering from pancreatic insufficiency, including cystic fibrosis patients. Similarly, any of these methods may be used to treat any cystic fibrosis patient.

Methods for treatment according to this invention include those which comprise the step of administering to a subject a therapeutically effective amount of a composition of this invention, wherein that therapeutically effective amount increases the coefficient of fat absorption in that subject by an amount between about 30% and about 35% over baseline, when the baseline coefficient of fat absorption in said subject is less than or equal to 40%. Preferably, the increase in the coefficient of fat absorption in such a subject is about 30% over baseline. In an alternate embodiment, methods for treatment comprise the step of administering to a subject a therapeutically effective amount of a composition of this invention, wherein that therapeutically effective amount increases the coefficient of fat absorption in that subject by an amount between about 10% and about 25% over baseline, when the baseline coefficient of fat absorption in that subject is greater than 40% but less than 85%. Preferably, the increase in the coefficient of fat absorption in such a subject is about 15% over baseline.

Additionally, methods for treatment according to this invention include those which comprise the step of administering to a subject a therapeutically effective amount of a composition of this invention, wherein that therapeutically effective amount increases the coefficient of nitrogen absorption in that subject by an amount between about 30% and about 35% over baseline, when the baseline coefficient of nitrogen absorption in that subject is less than or equal to 40%. Preferably, the increase in the coefficient of nitrogen absorption in such a subject is about 30% over baseline. In an alternate embodiment, methods for treatment comprise the step of administering to a subject a therapeutically effective amount of a composition of this invention, wherein that therapeutically effective amount increases the coefficient of nitrogen absorption in that subject by an amount between about 10% and about 25% over baseline, when the baseline coefficient of nitrogen absorption in that subject is greater than 40% but less than 85%. Preferably, the increase in the coefficient of nitrogen absorption in that subject is about 15% over baseline.

In another embodiment, methods of treatment according to this invention include those which comprise the step of administering to a subject a therapeutically effective amount of a composition of this invention, wherein that therapeutically effective amount increases carbohydrate absorption in that subject to a degree that is greater than or equal to about 10% over baseline. In another embodiment, such methods include those wherein the therapeutically effective amount of a composition of this invention is one which increases carbohydrate absorption in that subject to a degree that is greater than or equal to about 20% over baseline. As measured herein, a 10% increase in carbohydrate absorption constitutes an extra 90 calories per day. After 365 days, a total of 32,850 additional calories per year would be absorbed. Because it takes approximately 3,500 calories to gain a pound, a little over 9 pounds per year would thus be gained based on a 10% increase in carbohydrate absorption in a subject.

The compositions according to the present invention may be formulated for any conventional delivery route, including administration via the upper gastrointestinal tract, e.g., the mouth (for example in capsules, tablets, suspensions, or with food), or the stomach, or upper intestine (for example, by tube or infusion), oral route. Preferably, the compositions are formulated for oral delivery. Accordingly, the composition may be in any dosage form, including those of a solid, liquid, suspension or dispersion such as, for example, a capsule, tablet, caplet, sachet or dragee. For infants and children, or any adult who is unable to take tablets or capsules, the compositions are administered in liquid, suspension or sachet forms and may be administered with other compatible food or products.

In one embodiment of this invention, the compositions according to this invention are administered to a subject at the time of a meal or snack, in one or more capsules, suspensions or sachets. Preferably the compositions of this invention are administered to the subject in one to two capsules, suspensions or sachets per meal or snack. The compositions may be administered after one-half of the meal or snack has been consumed. A therapeutically effective amount of a composition for treating pancreatic insufficiency according to the present invention comprises lipase, protease and amylase in a ratio of about 1:1:0.15 USP units of enzyme activity and, per dose, comprises: an active lipase level of between about 5,000 USP units and about 100,000 USP units; an active protease level of between about 5,000 USP units and about 100,000 USP units; and an active amylase level of between about of between about 750 USP units and about 15,000 USP units. More preferably, such compositions comprise lipase, protease and amylase in a ratio of about 1:1:0.15 USP units of enzyme activity and, per dose, comprise: an active lipase level of between about 25,000 USP units and about 100,000 USP units; an active protease level of between about 25,000 USP units and about 100,000 USP units; and an active amylase level of between about 3,750 USP units and about 15,000 USP units. Most preferably, such compositions comprise lipase, protease and amylase in a ratio of about 1:1:0.15 USP units of enzyme activity and, per dose, comprise: an active lipase level of about 25,000 USP units; an active protease level of about 25,000 USP units; and an active amylase level of about 3,750 USP units.

For children, compositions according to this invention comprise lipase, protease and amylase in a ratio of about 1:1:0.15 USP units of enzyme activity and, per dose, comprise: an active lipase level of between about 12,500 USP units and about 25,000 USP units; an active protease level of between about 12,500 USP units and about 25,000 USP units; and an active amylase level of between about 1,875 USP units and about 3,750 USP units. For infants, such compositions comprise lipase, protease and amylase in a ratio of about 1:1:0.15 USP units of enzyme activity and, per dose, comprise: an active lipase level of between about 500 USP units and about 1,000 USP units; an active protease level of between about 500 USP units and about 1,000 USP units; and an active amylase level of between about 75 USP units and about 150 USP units. For all of the enzyme activity unit numbers and ranges discussed herein, one unit of lipase, protease or amylase is defined according to the assays set forth above for the respective enzyme. The above-described amounts are, respectively, also therapeutically effective amounts for treating malabsorption or maldigestion in adults, children or infants; or for increasing any of the coefficient of fat absorption, coefficient of nitrogen absorption, carbohydrate absorption or starch digestion in adults, children or infants.

The most effective mode of administration and dosage regimen of compositions according to this invention will depend on the effect desired, previous therapy, if any, the subject's health status or status of the condition itself, response to the therapy and the judgment of the treating physician.

Upon improvement of the subject's condition, a maintenance regimen may be adopted, as necessary. Subsequently, the dosage or frequency of administration, or both, may be reduced as a function of the symptoms, to a level at which the improved condition is retained. Subjects may, however, require intermittent treatment on a long-term basis upon any recurrence of the conditions or symptoms thereof.

In order that this invention may be better understood, the following examples are set forth. These examples are for the purpose of illustration only and are not to be construed as limiting the scope of the invention in any manner.

EXAMPLES

The following examples relate to compositions according to the present invention as well as clinical studies assessing their safety and efficacy for the treatment of pancreatic insufficiency. These studies included Phase 1 and Phase 2 clinical trials in cystic fibrosis patients suffering from pancreatic insufficiency.

The Phase 2 study assessed the efficacy of compositions according to this invention as measured by changes in: coefficient of fat absorption ("CFA"), coefficient of nitrogen absorption ("CNA"), oral carbohydrate absorption, stool weight per day, number of stools per day and quality of life, in terms of gastrointestinal symptoms, as measured by the Cystic Fibrosis Questionnaire ("CFQ"). The study also assessed the dosage of such compositions providing the highest degree of clinically meaningful coefficient of fat absorption improvement from baseline (off enzyme) in the subjects treated.

As demonstrated in the Phase 2 study, compositions according to the present invention provided a statistically significant increase in mean CFA and in CNA from baseline to the treatment period in cystic fibrosis subjects with pancreatic insufficiency. Compositions according to this invention were found to be efficacious at a minimal dose of 25,000 USP units of lipase, 25,000 USP units of protease and 3,750 USP units of amylase per capsule ("the middle dose" or "Arm 2" of the study); leading to a significant ($\geq$10%) increase in both CFA and CNA in most subjects. CFA and CNA also increased when the treatment dose contained lipase, protease and amylase in a ratio of 100,000:100,000:15,000 USP units of enzyme activity per capsule ("the higher dose" of "Arm 3" of the study). However, there was no statistical difference between the middle dose and higher dose regimens with respect to either CFA or CNA. Compositions according to this invention and used in the Phase 2 study also include those administered at a dose of 5,000 USP units of lipase, 5,000 USP units of protease and 750 USP units of amylase per capsule ("the low dose" or "Arm 1" of the study).

Advantageously, even after controlling for baseline values of CFA and CNA and gender of the subjects treated, this effect of the compositions according to this invention on CFA and CNA remained statistically significant (p=0.0003 and <0.0001, respectively, for the middle and higher dose treatment groups). When both CFA and CNA were examined as separate quartiles (FIGS. 1 and 2) the greatest changes were seen in those subjects with baseline values <40% and proportionally smaller changes in subjects with baseline CFA and CNA>40%. With respect to the CFA, the average increase in the middle dose treatment group of the eight subjects with a baseline CFA≦40% was 35.3%. The average increase in the higher dose group of 12 subjects with baseline CFA≦40% was 30.4%. The overall increase in CFA in 20 subjects with baseline CFA≦40%, for both the middle and higher treatment groups, was 32.3%.

The compositions according to this invention also produced a significant treatment effect as measured in terms of change in number and weight of stools per day in the subjects treated. The subjects receiving the higher dose exhibited a significant decrease in the number of stools from baseline to the treatment period, while stool weight decrease was statistically significant for both the middle dose and higher dose treatment groups. In fact there was highly significant inverse correlation (R=−0.7283; p<0.0001) between change in fat absorption and change in stool weight. In this respect, therefore, the higher dose (Arm 3) of the study did not differ significantly from the middle dose (Arm 2).

In all of the study subjects, although there were no overall statistically significant changes noted in the Starch Challenge Test on and off enzymes, the effect seen in the higher dose subjects in both maximum glucose change and area under the curve ("AUC") trended (p<0.057) in a direction that suggested amylase activity. In addition, an ad-hoc analysis using the Fischer Exact Test showed that more subjects in the middle dose group and in the higher dose group had a ≧10% increase in maximal glucose change following the Starch Challenge Test than the lower dose treatment group, based on a comparison of the off and on enzyme treatment periods (p=0.0138). These results demonstrate that amylase functions as an important component of the compositions of this invention, leading to improved starch digestion and carbohydrate absorption.

No serious adverse events were reported in subjects treated with the compositions according to this invention, which were well tolerated at all dose levels in the Phase 2 study. No subjects died over the course of this study.

Example 1

Preparation of the Study Compositions

The compositions used in the Phase 1 and Phase 2 studies discussed herein comprised lipase, protease, and amylase, each of which was manufactured separately under controlled conditions from different microbial strains prior to isolation, purification and drying. The manufacturing was carried out in such a way to provide compositions that would be stable and maintain potent enzyme activity within the small intestine.

Lipase: Methods for producing and purifying lipase from bacteria are well known to those skilled in the art. For example, the lipase component of the compositions was produced via fermentation from the bacterium *Burkholderia cepacia* (formerly known as *Pseudomonas cepacia*). Fermentation took place in a 25,000 liter fermenter. The strain was brought from a lyophilized frozen master cell bank, grown on a slant, brought up in eight liters of seed culture, further fermented in 2,500 liter seed fermenter, and finally produced in the 25,000 liter fermenter. After fermentation the viable organisms were killed by heat treatment and removed with centrifugation. The protein was concentrated by evaporation, followed by ethanol precipitation and washed with ethanol in a basket centrifuge.

A more purified lipase was generated by ammonium sulfate precipitation, adsorption and elution with DEAE cellulose, and subsequent refining, concentration and desalinization by ultra filtration. The resulting material was further purified by acetone treatment and CM-cellulose, and then glycine was added as a stabilization agent. The resulting material was filtered by membrane filtration and then lyophilized. The material was then sieved and analyzed for specific activity, purity and absence of pathogens.

The purified lipase was further processed by diafiltration in order to remove the glycine stabilizer. It was then precipitated and crystallized in 25% t-butanol, followed by crosslinking with $BS^3$ within the concentration ranges described supra, preferably so that the final concentration of crosslinker in the crosslinked lipase crystals was within the range between about 2.0 mM and about 5.0 mM. The crosslinked lipase crystals were washed with five volumes of 15% ethanol buffer followed by an additional wash of five volumes 15% ethanol buffer (with 1.5 mM calcium acetate, pH 5.0), in order to lower both residual crosslinker and t-butanol. The resulting material was lyophilized and packaged for shipment in HDPE bottles with tape closure, packed into one PE bag with a silica gel dessicant. Each batch was specifically analyzed for microbiological contamination with *Burkholderia cepacia* in addition to other microbes, and had to be negative for *Burkholderia cepacia* and pathogens before being released for clinical use.

Protease: Methods of producing and purifying protease are known to those skilled in the art. For example, the protease was produced by solid fermentation of *Aspergillus melleus*. The seed culture was brought up in solution, and then transferred onto the wheat bran. Once the seed had coated the sterilized bran, the solids were loaded onto trays for fermentation in fermentation rooms. After the fermentation was complete, the enzyme was extracted from the solid biomass by perfusion of water through large extraction tanks.

The extract containing protease was then run through charcoal beds and filtered to remove suspended particles. The solution was then concentrated and treated with charcoal a second time. The protease was precipitated with ethanol and then vacuum dried for final purification.

The protease was dissolved and then passed across an ion exchange resin. The material was then filtered prior to transfer into the crystallization tanks, where it was crystallized with multiple additions of ethanol. Once crystallization was complete, the crystals were recovered in a basket centrifuge and washed with additional ethanol. The crystals were recovered from the basket centrifuge and dried with forced air, followed by vacuum drying. Once dry the powder was transferred in bulk containers for final sieving and packaging.

Amylase: Methods of producing and purifying amylase are known to those skilled in the art. For example, amylase was produced by solid fermentation of *Aspergillus oryzae*. The seed culture was brought up in solution, and then transferred onto the wheat bran. Once the seed had coated the sterilized bran the solids were loaded onto trays for fermentation. After fermentation was complete, the enzyme was extracted from the solid biomass by perfusion of water through extraction tanks. The filtered extract was then concentrated and diafiltered. This diafiltration was followed by heat treatment and pH adjustment, followed by another diafiltration and concentration. Fish gelatin was then added to the material as a stabilizer prior to spray drying, and represents up to 30% of the total weight of the product. Once dried, the material was sieved, mixed with dextrin, and packaged. The dextrin was utilized as a stabilizer for long term storage and might represent as much as 30% of the total weight of the final product. The protein in the resulting active pharmaceutical ingredients was greater than 90% pure by SEC HPLC with detection at 280 nm. This 90% does not account for the presence of gelatin or dextrin as excipients; neither excipient had a significant absorbance at 280 nm. After being purified and processed, the lipase, protease and amylase were formulated together as capsules. More particularly, the dried enzymes were dry blended (with excipients) and filled into gelatin capsules. The compositions were referred to as TheraCLEC™.

Example 2

The Phase 2 Study

Treatment Doses

The compositions used in the Phase 2 study comprised active ingredients of crosslinked *Burkholderia cepacia* lipase crystals, *Aspergillus melleus* protease crystals and soluble *Aspergillus oryzae* amylase; and the following inactive ingredients: microcrystalline cellulose, Maltrin, Crospovidone, colloidal silicon dioxide, magnesium stearate and talc. They contained lipase, protease and amylase in a ratio of 1:1:0.15 USP units of enzyme activity.

The compositions were delivered in the form of capsules of two different strengths. The higher strength formulation, referred to as "TCT20", was filled into Size 2 white opaque, hard gelatin capsules at a strength of 20,000 USP Units of lipase, 20,000 USP Units of protease, and 3,000 USP Units of amylase. The lower strength formulation, referred to as "TCT5", was filled into Size 5 white opaque, hard gelatin capsules at a strength of 5,000 USP Units of lipase, 5,000 Units of protease, and 750 USP Units of amylase. The ratio of active to inactive ingredients on a w/w basis was 3:4 for TCT20 and 2:5 for TCT5.

Size 2 and Size 5 placebo capsules were used in the Phase 2 study to blind the TheraCLEC™ dose. Placebo capsules contained the same inactive ingredients as the TheraCLEC™ capsules and were of the same appearance as the TheraCLEC™ capsules, such that the capsule identity (active versus placebo) was unknown. The appropriate number and type of TheraCLEC™ capsules and placebo capsules were given to achieve the blinded dose level to which the subject was randomized.

During the Phase 2 study, in the approximate middle of each meal or snack during the 28-day Treatment Period, the subjects took a total of six capsules, which were a combination of TheraCLEC™ and placebo capsules, one was a size 5 capsule and five were size 2 capsules, as described below:

TABLE 1

Distribution of Study Treatment vs. Placebo by Treatment Arm

| | Number of Capsules per meal/snack | |
|---|---|---|
| Study Arm | Size 5 Capsules | Size 2 Capsules |
| Arm 1 | 1 TCT 5 | 5 Placebo |
| Arm 2 | 1 TCT 5 | 1 TCT 20 |
| | | 4 Placebo |
| Arm 3 | 1 Placebo | 5 TCT 20 |

Selection and Timing of Doses

The Phase 2 study's highest fixed dose of 100,000 USP Units of lipase/meal was equivalent to 1,250 lipase USP Units per kg for an 80 kg subject and 2,500 lipase USP Units per kg for a 40 kg subject.

TABLE 2

Dose of Study Drug-TheraCLEC ™

| | USP Units/meal or snack TheraCLEC ™ | | |
|---|---|---|---|
| Active Component | Arm 1 | Arm 2 | Arm 3 |
| Lipase | 5,000 | 25,000 | 100,000 |
| Protease | 5,000 | 25,000 | 100,000 |
| Amylase | 750 | 3,750 | 15,000 |

Further Parameters of the Phase 2 Study

The Phase 2 study was a randomized, double-blind, and parallel dose ranging trial. The study enrolled a total of 129 male and female subjects from approximately 26 US sites at three dose levels of TheraCLEC™ (approximately 42 subjects per arm). The study was separated into four distinct periods of observation and assessment: Screening, Baseline, Treatment and Follow-up.

The Phase 2 Study Population

The compositions prepared as described above were tested in three subject populations. The modified Intent-To-Treat ("mITT") population included all eligible subjects who underwent Baseline Period (off enzyme) measures, received at least one randomized dose, had Treatment Period assessments for safety, and had a marker-to-marker stool collection. Other subject populations were tested and the results were consistent with those of the mITT population.

Screening Period (Day S1-Baseline)

On day one of the screening visit (Day S1), subjects were interviewed to determine their eligibility for enrollment in the study. Subjects also underwent a complete physical exam.

Subjects were asked to eat a high fat diet throughout the study period. Subjects were permitted to take medications required for the treatment and management of their underlying cystic fibrosis and related illnesses. Subjects were not to receive enzyme supplementation products or dietary aids that may have been construed as enzyme supplementation during the inpatient Baseline (Days B1-B3) and Treatment (Days T1-T28) periods of the study.

Subjects were randomized to one of three blinded doses of TheraCLEC™.

Baseline Period (Days B1-B3)

Within 10-14 days of the Screening Visit, randomized subjects were required to enter an inpatient facility in a fasting state and prior to the first meal of the day (breakfast). The Baseline Period began with the first meal of the day (breakfast) on Day B1. Prior to breakfast, body weight was obtained. The subject then began a 72-hour controlled diet period without pancreatic enzyme supplementation. A stool marker (500 mg FD&C Dye Blue #2) was taken at the beginning of the first meal on Day B1. Fat and protein intake were recorded based on actual consumption. Stool collection for fecal fat and nitrogen assessments began after the first marker had passed (the stool containing the first marker was discarded) and ended when the second marker was first noticed in the stool (the stool containing the second marker was collected).

On each day of the Baseline Period, the subject were assessed for adverse events and concomitant medications, vital signs were recorded, and an abridged physical exam was performed.

Treatment Period (Days T1-T28)

The first dose of study drug was provided to each subject on day one of the treatment period (T1) in the approximate middle of the first meal after completion of the pre-dose procedures and Starch Challenge Test on Day T1 (lunch). The subjects were then observed for at least 30 minutes after administration of the first dose. If the drug was well tolerated, the subjects then took the same dose of study drug in the approximate middle of each of 3 meals and 2 snacks on day T1 through 28 of the treatment period. In this study, the middle of a meal was defined as the time at which the subjects had consumed approximately one-half of the meal or snack.

On Day T29, subjects discontinued the study drug. During the Day T29/ET office visit, a complete physical exam was performed. The subjects were also assessed for adverse events.

Follow-Up Period (Day F7±2)

During the Follow-Up Period, subjects were maintained on a high fat diet and usual care enzymes as prescribed by their physician. The end of the Follow-Up Period office visit (Day F7±2) was scheduled to occur 7±2 days after completion of the Treatment Period (Day T29) visit. At this visit, the subjects underwent an abridged physical examination and were assessed for adverse events and concomitant medications.

Stool Analysis for Fat and Nitrogen

Stool for a spot fecal elastase test was collected during the Screening Visit to assess eligibility for the study. Each subject had stool testing at various times during the study for the presence of occult blood and white blood cells.

During the inpatient Baseline period and the inpatient Treatment period, an indicator marker (500 mg of FD & C Blue #2) was given at the beginning of the first meal of the controlled diet (breakfast), which consists of approximately 100 grams of fat and a minimum of approximately 2 grams of protein per kilogram of body weight per day. Actual fat and protein intake was to be recorded based on the amount of food consumed.

After 72 hours on the controlled diet, a second blue indicator marker was given to fasted subjects with the test meal for the Start Challenged Test. Stool collection for fecal fat and nitrogen assessments began after the first blue marker had passed and was completed when the second blue marker had passed. The collected stool was measured for stool weight and analysis of fat and nitrogen content. Seligson, D (ed), Standard Methods of Clinical Chemistry, Volume II, Fatty Acids in Stool, 1985, Academic Press, pp 34-39; Veldee Miss., Nutritional Assessment, Therapy, and Monitoring in Burtis Calif., Ashwood ER (eds). Tietz Textbook of Clinical Chemistry, $3^{rd}$ Ed., 1999, W. B. Sanders Co, pp 1385-86.

The coefficient of fat absorption (% CFA) was calculated manually by the site using two data points:

(1) fat consumption in g/24 hours as provided by the central research dietician, and (2) fat excretion in g/24 hours as provided by Mayo Clinical Laboratory Services.

The CFA was calculated manually as follows:

$$\frac{(\text{Avg. grams of fat consumed}/24\text{ hours}-\text{Avg. grams of fat excreted}/24\text{ hours}) \times 100}{\text{Avg. grams of fat consumed}/24\text{ hours}}.$$

The coefficient of nitrogen absorption (% CNA) was calculated manually using two data points:

(1) nitrogen consumption in g/24 hours as provided by the central research dietician, and (2) nitrogen excretion in g/24 hours as provided by Mayo Clinical Laboratory Services.

The CNA was calculated manually as follows:

$$\frac{(\text{Avg. grams of nitrogen consumed}/24\text{ hours}-\text{Avg. grams of nitrogen excreted}/24\text{ hours})}{\text{Avg. grams of nitrogen consumed}/24\text{ hours} \times 100}.$$

Efficacy Evaluation—Coefficient of Fat Absorption

The coefficient of fat absorption at baseline, at treatment, and the change from baseline to treatment was summarized by treatment group. The coefficient of fat absorption reported was the mean of two independent CFA calculations using two fecal fat results from one stool collection. The difference among the three treatment groups in mean coefficient of fat absorption during the treatment period was analyzed using a one-way analysis of variance. In order to assess the three possible pairwise comparisons while controlling for the overall 5% type I error rate, Tukey's studentized range test was used. The dependent variable included the measures while on treatment.

A linear regression analysis examining the simultaneous effects of treatment group and mean baseline CFA was also performed. The dependent variable again included the on treatment period measures. Additional factors that were tested in the model included the following baseline measures: age, gender, race, and BMI. For these additional factors, a step-down process was used to eliminate non-significant factors ($p>0.10$) from the model. Pairwise comparisons were also performed using Tukey's studentized range test in this linear regression analysis.

The coefficient of fat absorption (CFA) at baseline, at treatment, and the change from baseline to treatment for the mITT population is summarized below in Table 3 by treatment group. Across all three treatment populations, there was a significant increase in mean CFA from baseline to the treatment period. On-treatment CFA was significantly larger in both treatment arm 2 (the middle dose) and treatment arm 3 (the higher dose) than in treatment arm 1 (the low dose). In addition, treatment arms 2 and 3 exhibited the larger mean increase in CFA from off-enzyme to enzyme than treatment arm 1. While treatment arm 3 showed a consistent numeric advantage over treatment arm 2, this difference was not statistically significant.

TABLE 3

Mean Coefficient of Fat Absorption-Analysis of Variance

|  | Arm 1 (N = 39) | Arm 2 (N = 41) | Arm 3 (N = 37) | Total (N = 117) | p-value* |
|---|---|---|---|---|---|
| Baseline |  |  |  |  |  |
| N | 39 | 41 | 36 | 116 |  |
| Mean | 55.0 | 55.6 | 52.2 | 54.4 |  |
| (SD) | (17.54) | (20.29) | (19.14) | (18.94) |  |
| Treatment** |  |  |  |  |  |
| N | 39 | 41 | 37 | 117 |  |
| Mean | 56.2 | 67.0 | 69.7 | 64.3 | 0.0032 |
| (SD) | (18.16) | (18.08) | (17.86) | (18.81) |  |
| Change from Baseline to Treatment |  |  |  |  |  |
| N | 39 | 41 | 36 | 116 |  |
| Mean | 1.2 | 11.4 | 17.3 | 9.8 | 0.0005 |
| (SD) | (14.77) | (19.10) | (18.37) | (18.59) |  |
| Percent (%) Change from Baseline to Treatment |  |  |  |  |  |
| N | 39 | 41 | 36 | 116 |  |
| Mean | 5.6 | 42.7 | 45.9 | 31.2 | 0.0153 |
| (SD) | (32.15) | (95.46) | (53.51) | (68.69) |  |

*Overall p-value from analysis of variance
**On treatment results (using Tukey's studentized range test for pairwise comparisons):
Treatment Arm 1 vs Treatment Arm 2, mITT p-value = 0.0229.
Treatment Arm 2 vs Treatment Arm 3, mITT p-value = 0.7874.
Treatment Arm 1 vs Treatment Arm 3, mITT p-value = 0.0041.

If baseline CFA is broken down into quintiles from 0-100%, it is clear that all treatment arms had a more profound increase over baseline from 0-40% CFA than if the baseline CFA was above 40% (see FIG. 1). Moreover, the lower the baseline CFA, the greater the response to the treatment.

Efficacy Evaluation—Coefficient of Nitrogen Absorption

The coefficient of nitrogen absorption (CNA) at baseline (B1 to B3) and treatment for the mITT population are summarized below in Table 4, by treatment group. The coefficient of nitrogen absorption reported was the mean of two independent CNA calculations using two fecal nitrogen results from one stool collection. The difference between the three treatment groups in mean CNA was analyzed in the same manner as mean CFA.

Similar to the measurements of CFA, across all three treatment populations, there was a significant increase in mean CNA from baseline to the treatment period. In all three treatment populations, on-treatment CNA was significantly larger in both treatment arm 2 and treatment arm 3 than in treatment arm 1. In addition, treatment arms 2 and 3 exhibited the larger mean increase in CNA from off-enzyme to enzyme than treatment arm 1. While treatment arm 3 showed a consistent numeric advantage over treatment arm 2, this difference was not statistically significant.

TABLE 4

Mean Coefficient of Nitrogen Absorption-Analysis of Variance

|  | Arm 1 (N = 39) | Arm 2 (N = 41) | Arm 3 (N = 37) | Total (N = 117) | p-value* |
|---|---|---|---|---|---|
| Baseline |  |  |  |  |  |
| N | 39 | 41 | 36 | 116 |  |
| Mean | 60.6 | 58.8 | 56.8 | 58.8 |  |
| (SD) | (16.38) | (17.88) | (16.36) | (16.84) |  |
| Treatment** |  |  |  |  |  |
| N | 39 | 41 | 37 | 117 |  |
| Mean | 61.6 | 71.3 | 74.6 | 69.1 | 0.0009 |
| (SD) | (15.46) | (16.38) | (13.51) | (16.05) |  |
| Change from Baseline to Treatment |  |  |  |  |  |
| N | 39 | 41 | 36 | 116 |  |
| Mean | 1.1 | 12.5 | 17.5 | 10.2 | 0.0002 |
| (SD) | (14.89) | (18.37) | (18.00) | (18.33) |  |
| Percent change from Baseline to Treatment |  |  |  |  |  |
| N | 39 | 41 | 36 | 116 |  |
| Mean (SD) | 9.0 (48.83) | 37.6 (96.72) | 40.6 (45.04) | 29.0 (69.74) | 0.0883 |

*Overall p-value from analysis of variance
**On treatment results (using Tukey's studentized range test for pairwise comparisons):
Treatment Arm 1 vs Treatment Arm 2, mITT p-value = 0.0145.
Treatment Arm 2 vs Treatment Arm 3, mITT p-value = 0.6130.
Treatment Arm 1 vs Treatment Arm 3, mITT p-value = 0.0009.

Figure 2:
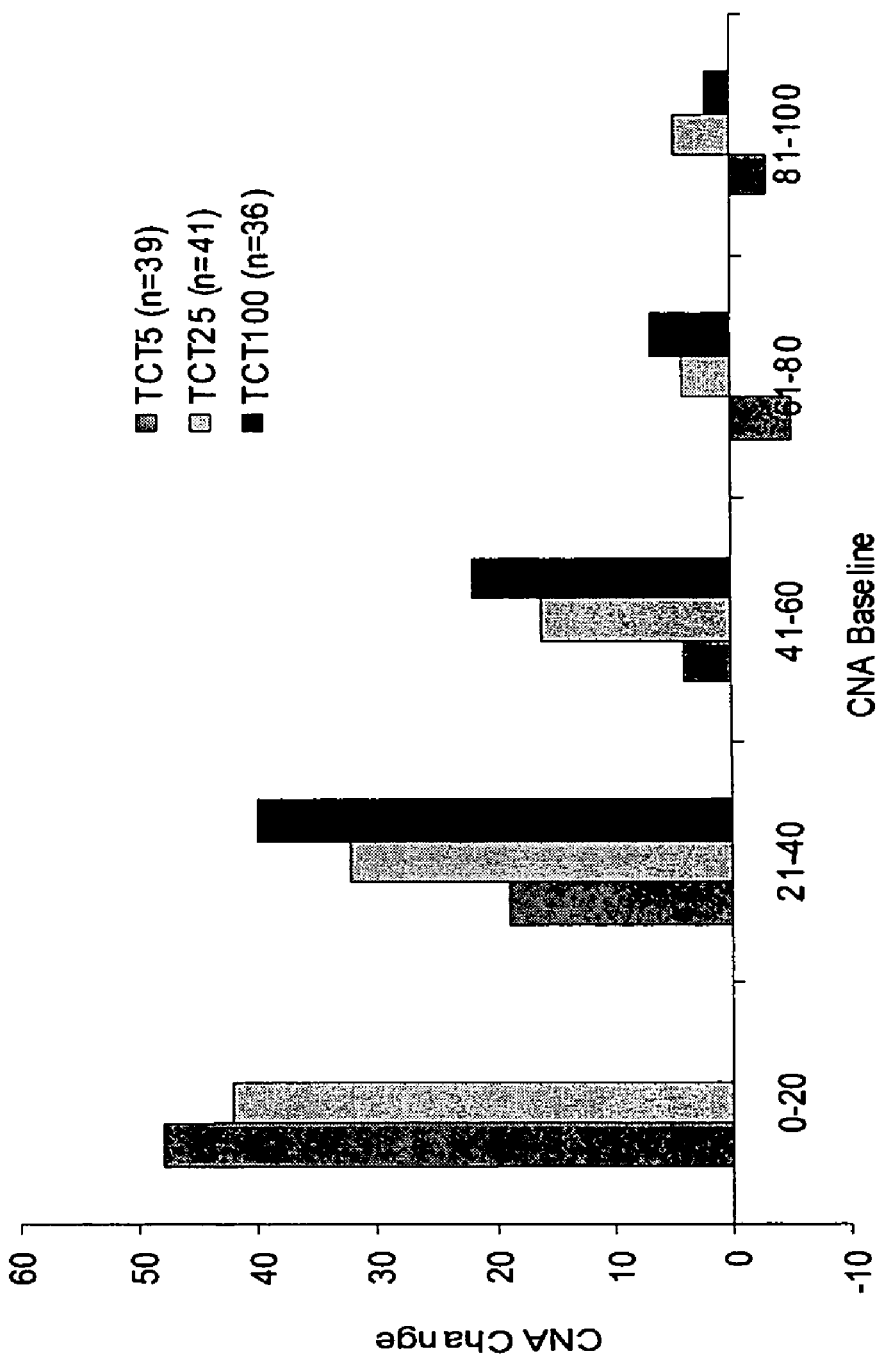
FIG. 2 illustrates the change in mean coefficient of nitrogen absorption ("CNA"), as compared to baseline, in patients treated with various compositions according to the present invention during a Phase 2 study.

If baseline CNA is broken down to quintiles from 0-100%, it is clear in FIG. 2 that all treatment groups had a greater increase over baseline if the baseline CNA was 40% or less than if baseline CNA was above 40%. Treatment arms 2 and 3 still appeared more effective than treatment arm 1. Moreover, the lower the baseline CNA, the greater the response to the treatment.

CFA and CNA Improvements and the Correlation Between Them

The study reflected a significant increase in mean CFA and in CNA from baseline to the treatment period in the middle and higher dose treatment groups among all three treatment populations. Moreover, treatment arm 3 (the higher dose treatment group) exhibited the largest mean increases in CFA and CNA during this time period, although, the difference between the middle and high dose was not statistically significant. Even after controlling for baseline values of CFA and CNA and gender, this treatment effect on CFA and CNA remained statistically significant (p=0.0003 and <0.0001, respectively).

Figure 3:
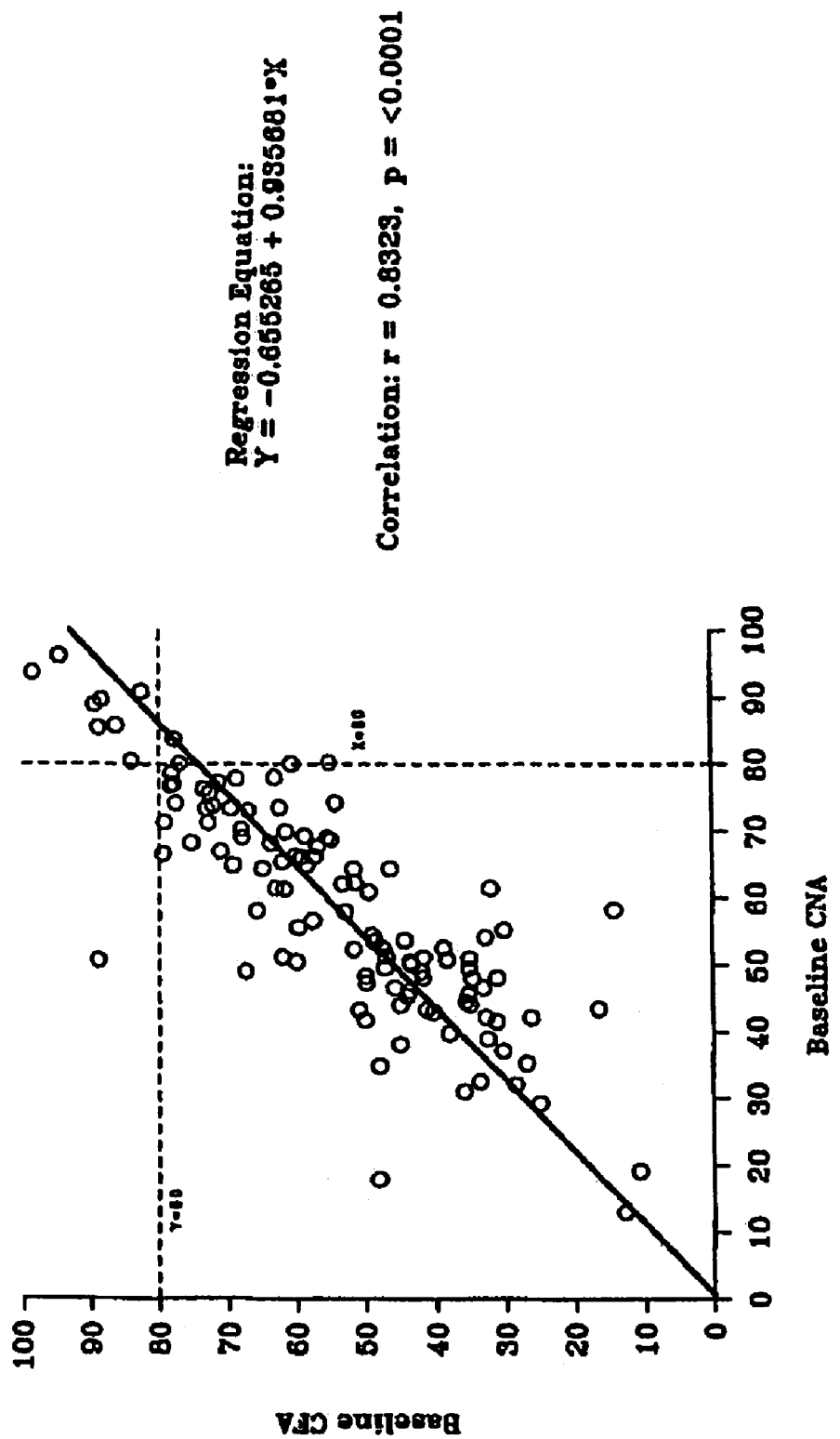
FIG. 3 illustrates the correlation between the coefficient of fat absorption ("CFA") and the coefficient of nitrogen absorption ("CNA") at baseline, in patients treated with compositions according to the present invention during a Phase 2 study.
Figure 4:
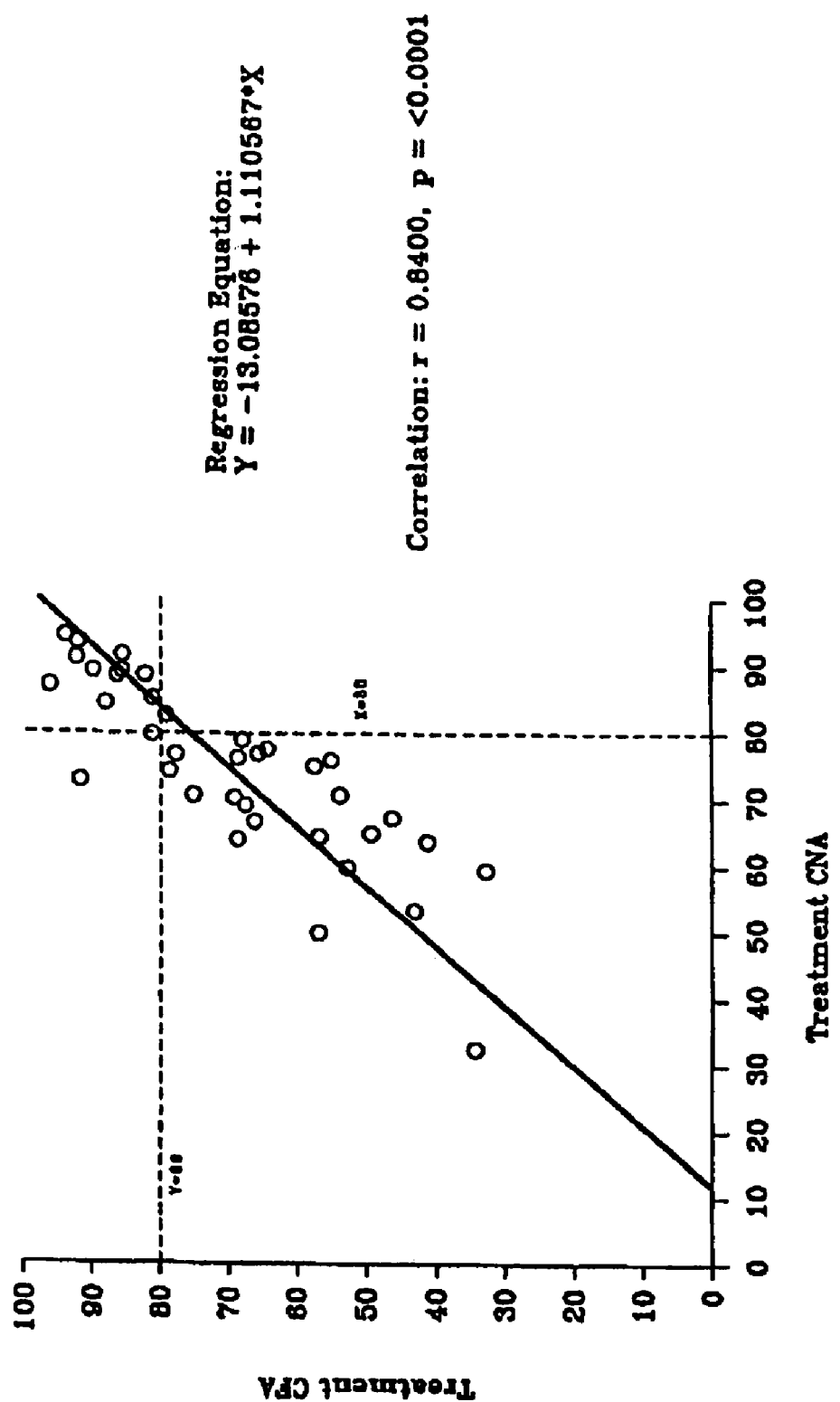
FIG. 4 illustrates the correlation between the coefficient of fat absorption ("CFA") and the coefficient of nitrogen absorption ("CNA") at treatment level, in patients treated with compositions according to the present invention during a Phase 2 study.
Figure 5:
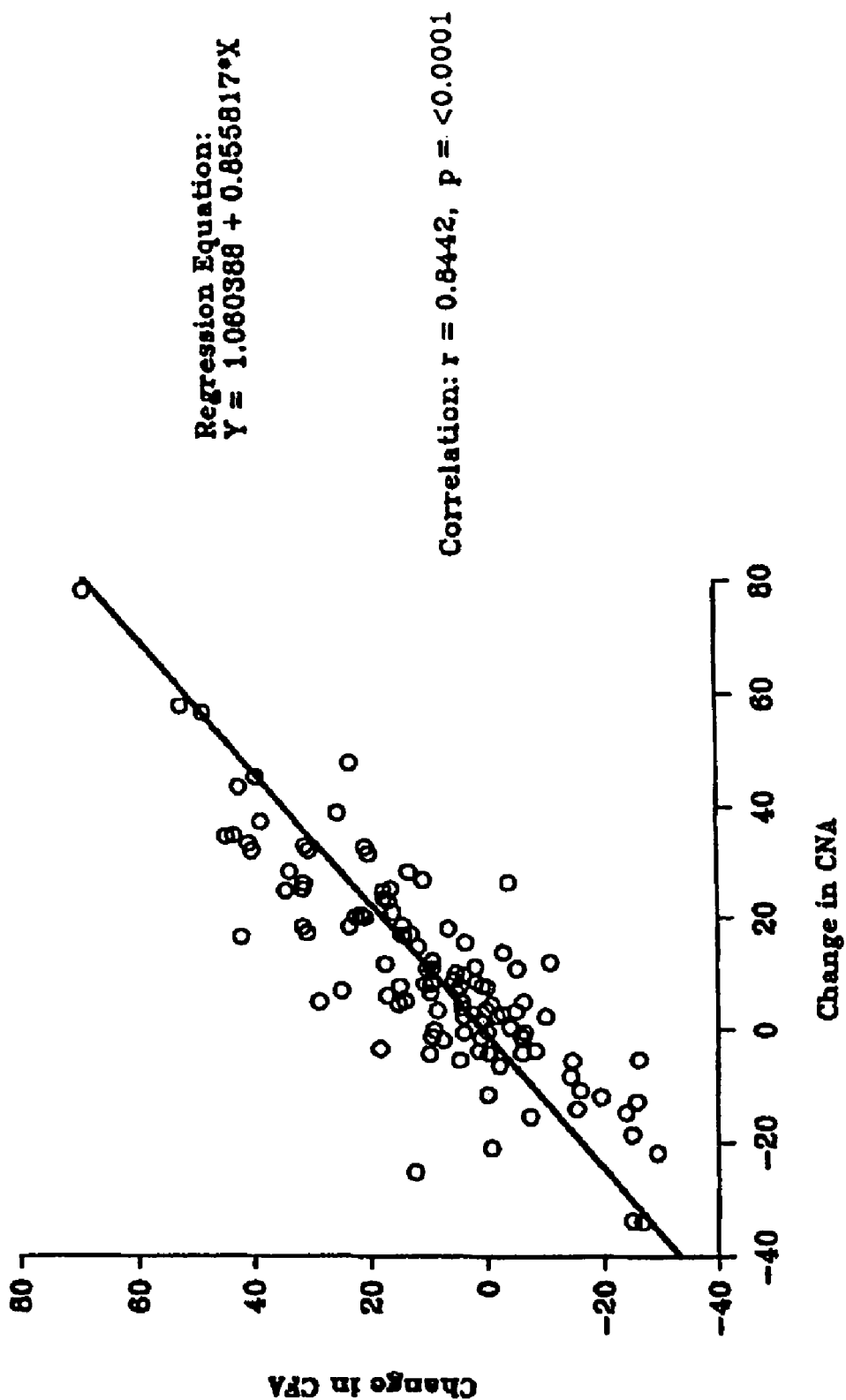
FIG. 5 illustrates the difference between the correlation between the coefficient of fat absorption ("CFA") and the coefficient of nitrogen absorption ("CNA") at treatment and baseline levels, in patients treated with compositions according to the present invention during a Phase 2 study.

The correlation between the increases in CFA and CFA were also statistically significant. FIGS. 3 and 4 illustrate the correlation between CFA and CNA in the mITT patients treated with all dose compositions according to the present invention at baseline level and treatment level, respectively. FIG. 5 illustrates the difference between the correlation between the CFA and the CNA at treatment and baseline levels in those patients.

Efficacy Evaluation—Change from Baseline Analysis—Stool Sampling

The mean changes in the number of stools and stool weights from baseline to the treatment periods against the relevant treatment period endpoint value are displayed separately for each study treatment group in Table 5 and Table 6, respectively.

In all three treatment arms, there was a decrease in number of stools from baseline to the treatment period (p=0.0968, p=0.0975, and p=0.1807, respectively). Treatment arm 3, in particular, exhibited the largest mean decrease (−0.2.6 in the mITT) in number of stools from baseline to treatment (p=0.0003). However, a between-groups comparison in the change in the number of stools revealed no statistically significant difference between the treatment arms.

There was also a significant decrease in weight of stools from baseline to treatment in the middle and higher treatment groups of all three treatment populations (p=0.0001). While treatment arm 3 of all three populations displayed the largest mean decrease in stool weight from baseline to treatment (p<0.0001), pairwise comparisons using Tukey's studentized range test revealed no statistically significant differences between the middle and higher treatment arms.

TABLE 5

Change in Number of Stools from Baseline to Treatment

| | Arm 1 (N = 39) | Arm 2 (N = 41) | Arm 3 (N = 37) | Total (N = 117) | p-value* |
|---|---|---|---|---|---|
| Baseline | | | | | |
| N | 39 | 41 | 37 | 117 | |
| Mean | 7.7 | 8.2 | 8.8 | 8.3 | |
| (SD) | (3.04) | (3.49) | (4.56) | (3.73) | |
| Treatment | | | | | |
| N | 39 | 41 | 37 | 117 | |
| Mean | 6.9 | 7.4 | 6.2 | 6.9 | |
| (SD) | (3.06) | (4.37) | (3.01) | (3.56) | |
| Change from Baseline to Treatment | | | | | 0.0968 |
| N | 39 | 41 | 37 | 117 | |
| Mean | −0.8 | −0.9 | −2.6 | −1.4 | |
| (SD) | (3.39) | (4.52) | (4.04) | (4.07) | |
| Paired t-test** | 0.1393 | 0.2211 | 0.0003 | 0.0003 | |

*Overall p-value from analysis of variance.
**Paired t-test.
Note:
Change from baseline results (using Tukey's studentized range test for pairwise comparisons):
Treatment Arm 1 vs Treatment Arm 2, mITT, p-values = 0.5502.
Treatment Arm 2 vs Treatment Arm 3, mITT, p-values = 0.4842.
Treatment Arm 1 vs Treatment Arm 3, mITT, p-values = 0.2040.

TABLE 6

Change in Stool Weight (grams) from Baseline to Treatment

| | Arm 1 (N = 39) | Arm 2 (N = 41) | Arm 3 (N = 37) | Total (N = 117) | p-value* |
|---|---|---|---|---|---|
| Baseline | | | | | |
| N | 38 | 41 | 36 | 115 | |
| Mean | 1234.0 | 1251.8 | 1396.8 | 1291.3 | |
| (SD) | (529.46) | (474.14) | (613.79) | (539.16) | |
| Treatment | | | | | |
| N | 38 | 41 | 37 | 116 | |
| Mean | 1174.1 | 937.3 | 869.2 | 993.2 | |
| (SD) | (565.34) | (539.91) | (448.92) | (533.10) | |
| Change from Baseline to Treatment | | | | | 0.0001 |
| N | 38 | 41 | 36 | 115 | |
| Mean | −59.9 | −314.5 | −514.2 | −292.9 | |
| (SD) | (399.46) | (455.89) | (428.37) | (463.44) | |
| Paired t-test** | 0.3612 | <0.0001 | <0.0001 | <0.0001 | |

*Overall p-value from analysis of variance.
**Paired t-test.
Note:
Change from baseline results (using Tukey's studentized range test for pairwise comparisons):
Treatment Arm 1 vs Treatment Arm 2, mITT, p-value = 0.8842.
Treatment Arm 2 vs Treatment Arm 3, mITT, p-value = 0.2415.
Treatment Arm 1 vs Treatment Arm 3, mITT, p-value = 0.1971.

Efficacy Evaluation—Starch Digestion and Carbohydrate Absorption as Measured by Blood Glucose Response In the Starch Challenge Test, subjects who had fasted overnight for at least 8 hours ingested a standard test meal comprising 100 grams of white flour bread (50 g carbohydrate) during the inpatient Baseline Period and the inpatient Treatment period. Subjects were to rest for 30 minutes before the Start Challenge Test began and activity was to have been limited during the evaluation. Blood glucose levels were measured with a glucometer (Accucheck, Bayer). A measurement was taken immediately before the test meal. TheraCLEC™ was administered approximately half-way through bread meal. Serial glucometer measures were taken over a 4-hour period. Calculated values include maximum glucose change from fasting level and On-Off enzyme maximum glucose change (T17-T1). Subjects with diabetes mellitus did not have the Starch Challenge Test performed if the fasting glucose measurement was less than 75 mg/dL.

Blood glucose response was measured by the following variables in the mITT population:

Glucose Change from Time 0: The change in glucose at each of the time points from Time 0.

Maximum glucose response: The maximum glucose value post Time 0.

Maximum change in glucose response: Defined as the maximum response minus the glucose value at Time 0.

Time to peak glucose response ($T_{max}$): Defined as the hours from Time 0 to the maximum glucose change.

Descriptive statistics are presented for each of these variables by treatment group for the following:

1. Off TheraCLEC™

2. On TheraCLEC™

3. On TheraCLEC™ minus Off TheraCLEC™

4. On TheraCLEC™: Off TheraCLEC™ Ratio (R)

These descriptive statistics are presented both for all subjects and for subjects without diabetes only. A subject was considered having cystic fibrosis related diabetes if they had either a medical history of known diabetes, were on insulin or diabetes related oral medication or if they had a fasting glucose measurement ≧126 mg/dL or a postprandial glucose ≧200 mg/dL.

In Table 7, the 25 subjects with cystic fibrosis related diabetes mellitus have been removed from the analysis to reduce the variability from both high baseline glucose as well as decreases in glucose following the "Starch Challenge Test" as a result of morning insulin injections. TCT5 appears to have significantly (p=0.0053) less number of subjects with increases in maximum glucose on-off enzyme ≧10 mg/dL than TCT25. In addition, the results in Table 7 suggest that the middle range of amylase in Treatment Arm 2 is equally as effective as the highest dose in Treatment Arm 3.

TABLE 7

Starch Challenge Test in Non-Diabetic Patients with Cystic Fibrosis - looking at maximum glucose change on-off enzyme treatment

| Maximum Glucose Δ On-Off Enzyme | Treatment Arm 1: TCT5 | Treatment Arm 2: TCT25 | Treatment Arm 3: TCT100 |
|---|---|---|---|
| <10 mg/dl | 21 | 14 | 15 |
| >10 mg/dl | 4 | 16 | 11 |
| >20 mg/dl | 3 | 8 | 8 |

*Fisher's Exact (Overall): p = .0138
TCT5 vs. TCT25, p = 0.0053
TCT5 vs. TCT100, p = 0.0644
TCT25 vs. TCT100, p = 0.4357

Overall, this study demonstrated that subjects treated with compositions according to this invention achieved increased starch digestion and carbohydrate absorption, as measured by blood glucose response, with those subjects in the higher dose treatment group requiring less time to do so.

Example 3

The Phase 1 Study

Prior to the Phase 2 study, compositions according to this invention were also assessed for their safety and preliminary efficacy in a Phase 1 trial in cystic fibrosis patients suffering from pancreatic insufficiency.

An open label, dose-ranging study was carried out to determine the acute safety, tolerability and clinical activity of TheraCLEC™ in 23 cystic fibrosis patients afflicted with pancreatic insufficiency. Subjects took either 100, 500, 1,000, 2,500 or 5,000 lipase units/kg/meal of TCT for three days. Clinical and laboratory safety parameters and adverse events were monitored.

There were no serious adverse events or deaths in the Phase 1 study. Most adverse events were mild, although gastrointestinal complaints were common. TheraCLEC™ increased the coefficient of fat absorption and the coefficient of nitrogen absorption in all groups except those receiving 100 lipase units/kg/meal. For all subjects at the other dosing levels, the mean CFA increase=20.6±23.5, mean CNA increase=19.7±12.2% and mean stool weight decreased=425±422 grams.

TheraCLEC™ was well-tolerated in this short-term exposure study at doses up to 5,000 lipase units/kg/meal. Preliminary efficacy data demonstrated a beneficial effect on fat and nitrogen absorption. Advantageously, these effects were seen with a dosage of 500 lipase units/kg/meal and there appeared to be no need to increase the dose beyond that level to achieve these results. These data supported a larger randomized Phase 2 trial.

1. The Phase 1 Study Design

An open label, multicenter, dose-ranging study was carried out, with a primary aim to determine the acute safety and tolerability of five dose levels of TheraCLEC™, in pancreatic-insufficient subjects with cystic fibrosis. Secondary aims were to determine the effect of TheraCLEC™ on oral fat and nitrogen absorption, gastrointestinal symptoms, and the number and weight of stools. TheraCLEC™ had fixed proportions of lipase, amylase and protease. Dosing cohorts were based on lipase dose per kg per meal, as shown in Table 8.

TABLE 8

Dosing cohorts

| Active Component | USP units/kg/meal | | | | |
|---|---|---|---|---|---|
| | Cohort 1 | Cohort 2 | Cohort 3 | Cohort 4 | Cohort 5 |
| Lipase | 500 | 1,000 | 2,500 | 5,000 | 100 |
| Protease | 500 | 1,000 | 2,500 | 5,000 | 100 |
| Amylase | 75 | 150 | 375 | 750 | 15 |

Provided as capsules with the following enzymes in fixed proportions: lipase 20,000 USP units+protease 20,000 USP units+amylase 3,000 USP units per capsule).

Subjects with cystic fibrosis followed at one of eleven CF Foundation-accredited centers were recruited for this study. All individuals signed a consent form approved by the local Institutional Review Board, and in the case of pediatric patients, assent was also given. Subjects were included if they were ≧13 to ≦45 years of age, had a diagnosis of cystic fibrosis based upon standard criteria [B. J. Rosenstein et al., "The Diagnosis of Cystic Fibrosis: A Consensus Statement", *J. Pediatr.*, 132, pp. 589-595 (1998)], were pancreatic insufficiency based on fecal elastase <100 mg/gm measured at outpatient screening using the ScheBo monoclonal ELISA assay (BioTech USA) and had a coefficient of fat absorption ≦80% measured at inpatient screening, had forced expiratory volume in one second ($FEV_1$) ≧30% predicted, had a Body Mass Index >10th percentile, and were clinically stable with no evidence of acute upper or lower respiratory tract infection. Subjects were excluded if they were pregnant or breastfeeding, had an episode of distal intestinal obstruction syndrome requiring intervention in the emergency room or hospital in the previous six months, were taking medications that alter gastric pH (e.g. histamine-2 receptor antagonists, proton pump inhibitors or antacids) in the previous week and were unable to discontinue these medications during the study, had a history of fibrosing colonopathy, allergic bronchopulmonary aspergillosis, or liver disease defined by the following criteria: twice-normal alanine aminotransferase (AST), aspartate aminotransferase (ALT), or alkaline phosphatase; history of variceal bleed; evidence of cirrhosis or significant liver disease on liver biopsy; liver transplant; subject has taken ursodeoxycholic acid in the year prior. Subjects unable to discontinue enteral tube feedings during the inpatient portions of the study protocol, those with known food additive hypersensitivity, or those who had participated in any other investigational study of a drug, biologic, or device not currently approved in the prior month were also excluded.

If subjects met criteria at the initial screening visit, they were admitted to a clinical research center. The subject's prescribed enzyme therapy was discontinued, an indicator dye marker (FD & C Blue #2 500 mg) was given orally, and the subject was placed on a special diet consisting of 100 grams of fat and a minimum of 2 grams of protein per kilogram of body weight per day divided in three meals and two snacks. Actual fat and protein intake were recorded based on the amount of food consumed. After 72 hours on the special diet, the diet was discontinued and a second indicator marker was given. Patients resumed their normal enzyme therapy at this time. Stool collection for fecal fat and nitrogen assessments began after the first stool in which the blue marker was seen, and was completed when the second marker was passed, with that stool included in the collection. CFA was calculated, and if it was ≦80%, the subject was eligible for the treatment phase of the study.

Subjects were again admitted to a clinical research center and routine pancreatic enzyme supplementation was discontinued. The dye marker and special diet were provided, and subjects took the study medication with each of three meals and two snacks for the following 72 hours, with doses per cohort as previously described. Subjects were instructed to take the study medication before each meal. After 72 hours, the special diet was discontinued and a second indicator marker was given. Patients resumed their normal enzyme therapy at this time. The procedure for stool collection was the same as described above. A follow-up phone call was made within three days of discharge from the clinical research center and a follow-up visit occurred three to seven days post-discharge.

Safety monitoring included the incidence of adverse events, as determined by open ended questioning of study subjects during outpatient visits and inpatient care and during the scheduled phone call, frequency of abnormal laboratory tests including routine hematologic, serum chemistry, and coagulation profiles, urinalysis, urinary uric acid excretion, and stool heme and white blood cell assay. Also monitored was the frequency of gastrointestinal symptoms as measured by a GI-specific modified Cystic Fibrosis Questionnaire (CFQ) [A. Quittner et al., "CFQ Cystic Fibrosis Questionnaire, a Health Related Quality of Life Measure", English Version 1.0. (2000)].

The CF Foundation's Therapeutics Development Network Data Safety and Monitoring Board (DSMB) provided oversight for this trial. The DSMB monitored safety data of escalating dose cohorts throughout the trial and formal evaluation of safety was required before subjects could be enrolled in the 5,000 lipase units/kg/meal cohort, since this exceeds current dosing recommendations. The DSMB was also charged with stopping the trial at any time for concerns of subject safety.

2. The Phase 1 Composition

The three enzymatic components of TheraCLEC™, lipase, protease, and amylase, were manufactured independently. The lipase was derived via fermentation from the bacterium *Burkholderia cepacia* (formerly known as *Pseudomonas cepacia*), and was then processed to form lipase crystals which were subsequently crosslinked, creating an enzyme form stable to acid and proteases without enteric coating (referred to as TheraCLEC™-lipase). Each batch was specifically cultured for microbiological contamination with *Burkholderia cepacia* and must be negative for *Burkholderia cepacia* for release of the batch for clinical use. The protease component was derived from *Aspergillus melleus*; the amylase component was derived from fermentation of *Aspergillus oryzae*. Similarly, these products underwent through multiple purification steps after which they were cultured for total mold and yeast.

The three enzyme components comprising TheraCLEC™ were formulated as a powder-containing capsule. Preclinical efficacy studies demonstrated that lipase and protease were efficacious at the dose of ≧500 lipase unit/kg/meal and ≧1000 protease unit/kg/meal in the pancreatic insufficient dog model. In vitro analysis of the *Aspergillus*-derived amylase in TheraCLEC™ was performed using both USP and FCC (Food Chemical Codex) methodology (which is equivalent to the USP methodology used for testing drugs). Fungal amylase has a different pH profile than porcine-derived amylase. Fungal amylase is twenty times more active at pH 4.8 than porcine amylase. Thus, a dose of amylase twenty times lower than would be found relative to lipase in a standard pancrelipase capsule was chosen for TheraCLEC™.

3. Analysis of Data in The Phase 1 Study

The coefficient of fat absorption was calculated as follows:

$$\frac{(\text{grams of fat consumed} - \text{grams of fat excreted}) \times 100}{\text{grams of fat consumed}}$$

The same equation using the number of grams of nitrogen was used to calculate the coefficient of nitrogen absorption (CNA).

We planned to summarize demographic and prognostic characteristics including age, gender, race, genotype, pulmonary function, and spot fecal elastase by dosing cohort and overall. The sample size for this Phase 1 study was estimated to be 20 subjects, 4 subjects per dosing cohort. The study was not powered for formal statistical testing. We planned to group adverse events using a standard classification system. The frequency of abnormal laboratory values was tabulated by study period, time point, and dose cohort.

4. Results of the Phase 1 Study

Twenty-three subjects (14 M) were enrolled at 11 cystic fibrosis Centers. The mean age of subjects was 23.5±7.8 (SD) (range=15.2-44.5 years) (Table 9). One additional subject each was enrolled in cohorts 1, 3 and 5 as a result of several centers recruiting subjects simultaneously.

TABLE 9

Study Demographics

| Number of Patients | | Age (n = 23) | |
|---|---|---|---|
| | | Parameter | Years |
| Planned | 20 | Mean | 23.5 |
| Enrolled | 23 | Standard Deviation | 7.8 |
| Discontinued from study drug | 0 | Min-Max | 15.2-44.5 years |

| Race (n = 23) | | Gender (n = 23) | |
|---|---|---|---|
| Parameter | N (%) | Parameter | N (%) |
| Caucasian | 22 (95.7%) | Male | 14 (61%) |
| Black | 0 (0.0%) | Female | 9 (39%) |
| Asian | 0 (0.0%) | | |
| Hispanic | 0 (0.0%) | | |
| Other | 1 (4.3%) | | |

5. Safety

TheraCLEC™ was well-tolerated at all dose levels. No serious adverse events or deaths were documented and there were no patient withdrawals during the study. During the pre-treatment period off enzyme therapy the most commonly affected body system was gastrointestinal, with 14 subjects reporting a total of 23 pretreatment adverse events. The most common pretreatment gastrointestinal adverse events were abdominal discomfort (4 subjects reporting 5 events), upper abdominal pain (4 subjects reporting 4 events), and flatulence (4 subjects reporting 4 events). The second most commonly affected body system was the respiratory system, with 5 subjects reporting 8 pretreatment adverse events. The most common pretreatment respiratory adverse event was cough (4 subjects reporting 4 events).

Treatment-emergent adverse events beginning after day 2 occurred in 18 (78.3%) of the 23 subjects. There were no statistically significant differences among the cohorts in the incidence of treatment-emergent adverse events (p=0.6196).

There were 11 (47.8%) subjects with related adverse events (defined as events classified by the Investigator as possibly or probably related to study medication).

Six subjects experienced increases in alanine aminotransferase (ALT) and/or aspartate aminotransferase (AST) during the study. Four subjects had elevated enzyme levels that began following study drug treatment. One subject (Cohort 1) had a high ALT level at the end of study visit and one subject (Cohort 5) had elevated AST at the follow-up assessment on the follow-up visit.

6. Efficacy

Figure 6:
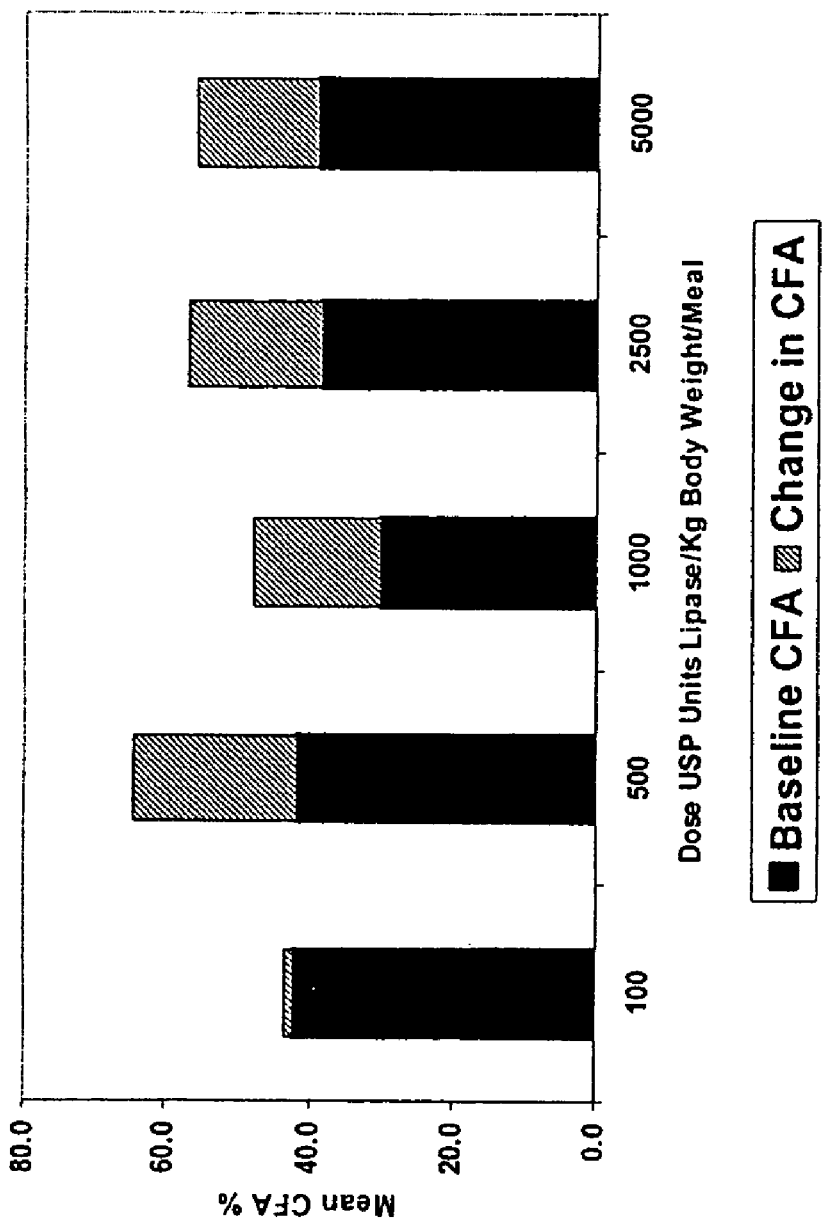
FIG. 6 illustrates the change in mean coefficient of fat absorption ("CFA"), as compared to baseline, in cystic fibrosis patients treated with various doses according to the present invention during a Phase 1 study.
Figure 7:
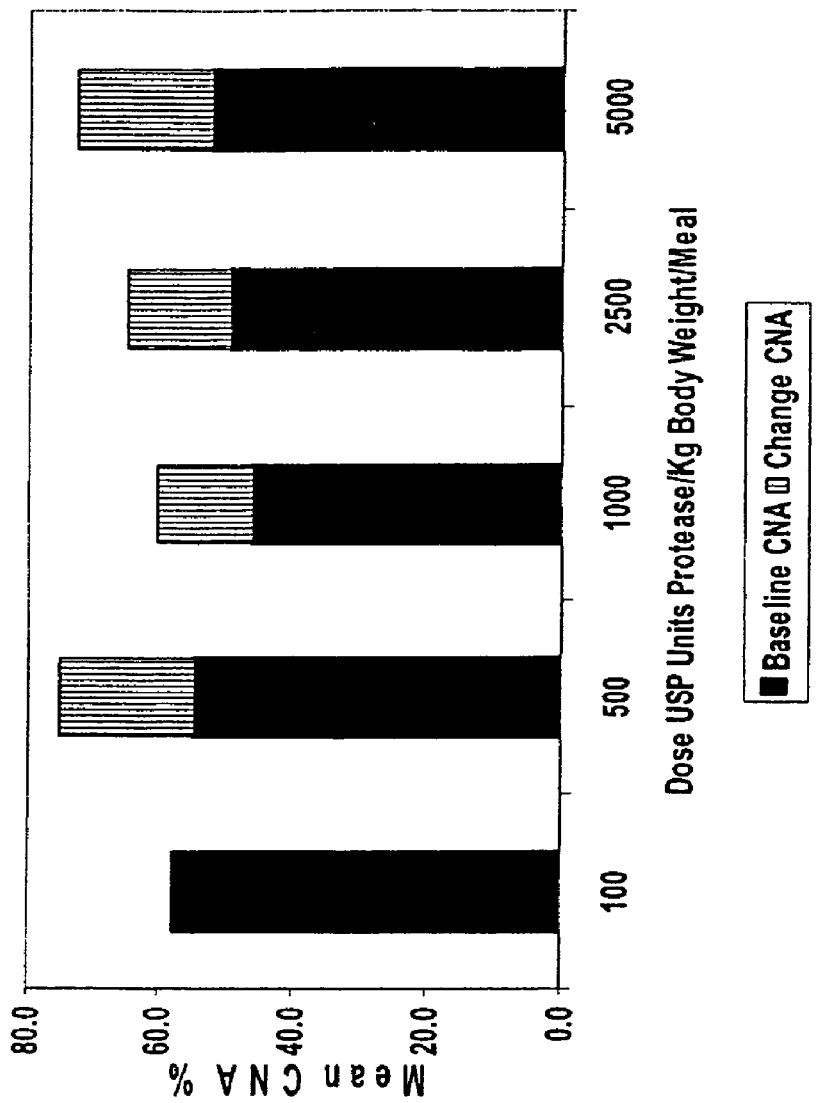
FIG. 7 illustrates the change in mean coefficient of nitrogen absorption ("CNA"), as compared to baseline, in patients treated with various doses according to the present invention during a Phase 1 study.

As summarized in Table 10 and FIGS. 6 and 7, the preliminary clinical activity data in Cohorts 1-4 demonstrate that treatment with TheraCLEC™ increased CFA and CNA when compared to the period off all pancreatic enzyme supplementation. For all subjects in Cohorts 1-4, the mean increase in CFA was 20.6±23.5% and mean CNA increased 19.7±12.2%. Stool weight was also decreased following treatment with TheraCLEC™ for these cohorts with an average decrease of 425±422 grams. CFA and CNA were minimally increased over the off enzyme levels at the lowest TheraCLEC™ dose level (Cohort 5:100 USP units lipase/kg/meal, 100 USP units protease/kg/meal, and 15 USP units amylase/kg/meal).

was large. Values for CFA in this study appear to be lower than those in the published literature. Possible explanations include selection bias, diet, complete collections and timing of enzymes.

All subjects in this study had severe pancreatic insufficiency, as determined by screening fecal elastase and corroborated by CFA off enzymes. Other studies have included pancreatic sufficient patients, which will shift mean CFA's higher [R. C. Stern et al., "A Comparison of the Efficacy and Tolerance of Pancrelipase and Placebo in the Treatment of Steatorrhea in Cystic Fibrosis Patients with Clinical Exocrine Pancreatic Insufficiency", *Am J. Gasteroenterol.*, pp. 1932-1938 (2000); M. P Francisco et al., "Ranitidine and Omeprazole as Adjuvant Therapy to Pancrealipase to Improve Fat Absorption in Patients with Cystic Fibrosis", *J. Pediatr. Gastrenterol. Nutr.*, 35, pp. 79-83 (2002)].

In this study, subjects took in at least 100 grams of fat per day. CFA's reported in the literature that were carried out based on the patient's routine diet likely were based on a lower fat intake, since many ambulatory patients take in less than 100 grams of fat per day [P. Durie et al., "Uses and Abuses of Enzyme Therapy in Cystic Fibrosis", *J. Royal Soc. Med.*, 91, suppl. 34, pp. 2-3 (1998); D. A. Kawchak et al.,

TABLE 10

Clinical Activity of TheraCLEC ™:
Change from Screening Period to Treatment Period

| Change from Baseline | Cohort 1 (N = 5) | Cohort 2 (N = 4) | Cohort 3 (N = 5) | Cohort 4 (N = 4) | Cohort 5 (N = 5) | Total (N = 23) |
|---|---|---|---|---|---|---|
| CFA[1] Mean (SD) | 22.7% (19.4) | 17.7% (25.9) | 18.9% (11.9) | 17.2% (42.3) | 1.2% (20.3) | 15.4% (23.8) |
| CNA[2] Mean (SD) | 20.3% (14.2) | 14.4% (18.0) | 15.8% (5.7) | 20.6% (16.5) | 0.1% (4.1) | 14.0% (13.7) |
| Number of Stools Mean (SD) | −1.2 (1.5) | −0.8 (1.7) | −2.6 (1.7) | −2.8 (2.6) | 0.2 (3.3) | −1.4 (2.4) |
| Stool Weight Mean weight (gm) of stools (SD) | −311.4 (371.7) | −308.8 (367.5) | −613.2 (423.3) | −836.0 (284.7) | −116.8 (373.2) | −425.5 (422.2) |

SD = standard deviation
[1]Coefficient of fat absorption = 100 * (number of grams of fat consumed − number of grams of fat obtained)/(number of grams of fat consumed).
[2]Coefficient of nitrogen absorption − 100 * (number of grams of nitrogen consumed − number of grams of nitrogen obtained)/(number of grams of nitrogen consumed).

Results of the Phase 1 Study

TheraCLEC™ appeared to be safe and well-tolerated in this three-day exposure study. There was no dose-relation in treatment-emergent adverse events. Gastrointestinal complaints were frequent during this study, whether subjects were on usual care, off enzymes, or on TheraCLEC™, although they occurred with lowest frequency during the outpatient period when subjects were on usual care. During the inpatient portions of the study, subjects were queried about GI complaints on a regular basis, and the study was unblinded, thus creating bias. Elevations of liver enzymes and the presence of both heme and white blood cells in stool were no more common when subjects were on TheraCLEC™ than when they were off enzymes or on usual care.

There was improved absorption of fat and nitrogen on TheraCLEC™ compared to baseline, demonstrating efficacy of the lipase and protease components of TheraCLEC™. There did not appear to be a dose-response curve at doses above 500 lipase units/kg/meal. Although there was a trend towards lower fecal weight with increasing doses, the range "Longitudinal, Prospective Analysis of Dietary Intake in Children with Cystic Fibrosis", *J. Pediatr.*, 129, pp. 119-129 (1996)]. A lower fat load may be more easily handled by the residual, compensatory lingual lipase seen in patients with cystic fibrosis [B. Fredrikzon et al., "Lingual Lipase: an Important Lipase in the Digestion of Dietary Lipids in Cystic Fibrosis?", *Pediatr. Res.*, 14, pp. 1387-1390 (1980)].

A blue food dye was used to mark the stool collection. Anecdotally, clinical research center nurses have reported that carmine red or charcoal markers can be difficult to identify in stool. FD&C Blue #2 at a dose of 500 mg orally is easily visible when passed in stool and clearly demarcates the start and end of the stool collection. A shortened collection of stool will result in less fat in the total stool collection, leading to a falsely high CFA. Previous studies may have had falsely higher CFAs because of difficulty in identifying the start and end of the collection. Since collecting stool is odious, there is a human tendency to end the collection as soon as possible.

Although the foregoing invention has been described in some detail by way of illustration and example for purposes of clarity and understanding, it will be readily apparent to those of ordinary skill in the art in light of the teachings of this invention that certain changes and modifications may be made thereto without departing from the spirit or scope of the disclosure herein, including the appended claims.

We claim:

1. A composition comprising crosslinked *Burkholderia cepacia* lipase crystals, *Aspergillus melleus* protease crystals, and amorphous *Aspergillus oryzae* amylase, wherein the ratio of lipase, protease and amylase in said composition is about 1:1:0.15 USP units.

2. The composition according to claim 1, wherein the lipase crystals are crosslinked with a multifunctional crosslinker.

3. The composition according to claim 2, wherein the multifunctional crosslinker is bis (sulfosuccinimidyl) suberate.

4. The composition according to claim 1, further comprising a pharmaceutically acceptable excipient.

5. The composition according to claim 1, wherein the composition is in an oral dosage form selected from the group consisting of tablets, capsules, tablets, slurries, sachets, suspensions and dragees.

6. The composition of claim 1, wherein the ratio of lipase, protease, and amylase is 1:1:0.15.

7. A method for treating malabsorption in a mammal comprising the step of administering to said mammal a therapeutically effective amount of a composition according to claim 1.

8. A method for treating pancreatic insufficiency in a mammal comprising the step of administering to said mammal a therapeutically effective amount of composition according to claim 1.

9. A method for increasing the coefficient of fat absorption and the coefficient of nitrogen absorption in a mammal comprising the step of administering to said mammal a therapeutically effective amount of composition according to claim 1.

10. The method according to claim 9, wherein the coefficient of fat absorption and the coefficient of nitrogen absorption are increased in said mammal by the same amount.

11. A method for increasing carbohydrate absorption in a mammal comprising the step of administering to said mammal a therapeutically effective amount of composition according to claim 1.

12. The method according to any one of claims 7, 8, 9 and 11, wherein the mammal suffers from cystic fibrosis.

13. The method according to any one of claims 7, 8, 9 and 11, wherein the therapeutically effective amount of said composition provides to said mammal about 25,000 USP units of lipase, about 25,000 USP units of protease and about 3,750 USP units of amylase.

14. The method according to any one of claims 7, 8, 9 and 11, wherein the therapeutically effective amount of said composition provides to said mammal about 100,000 USP units of lipase, about 100,000 USP units of protease and about 15,000 USP units of amylase.

15. The method according to claim 13 or 14, wherein the composition is administered to said mammal with each meal or snack.

16. The method according to any one of claims 7, 8 and 9, wherein the therapeutically effective amount of said composition increases the coefficient of fat absorption in said mammal by an amount between about 30% and about 35% over baseline coefficient of fat absorption in said mammal when said baseline is less than or equal to 40%.

17. The method according to any one of claims 7, 8 and 9, wherein the therapeutically effective amount of said composition increases the coefficient of nitrogen absorption in said mammal by an amount between about 30% and about 35% over baseline coefficient of nitrogen absorption in said mammal when said baseline is less than or equal to 40%.

18. The method according to any one of claims 7, 8 and 9, wherein the therapeutically effective amount of said composition increases the coefficient of fat absorption in said mammal by an amount between about 10% and about 25% over baseline coefficient of fat absorption in said mammal when said baseline is greater than 40% but less than 85%.

19. The method according to any one of claims 7, 8 and 9, wherein the therapeutically effective amount of said composition increases the coefficient of nitrogen absorption in said mammal by an amount between about 10% and about 25% over baseline coefficient of nitrogen absorption in said mammal when, said baseline is greater than 40% but less than 85%.

20. The method according to any one of claims 7, 8 and 11, wherein the therapeutically effective amount of said composition increases carbohydrate absorption in said mammal by an amount equal to or greater than about 10% over the baseline carbohydrate absorption in said mammal.

* * * * *